United States Patent
Sinfield et al.

(10) Patent No.: US 8,325,337 B2
(45) Date of Patent: Dec. 4, 2012

(54) TIME RESOLVED RAMAN SPECTROSCOPY

(75) Inventors: Joseph V. Sinfield, West Lafayette, IN (US); Oliver Colic, Palo Alto, CA (US)

(73) Assignee: Purdue Research Foundation, West Lafayette, IN (US)

( * ) Notice: Subject to any disclaimer, the term of this patent is extended or adjusted under 35 U.S.C. 154(b) by 245 days.

(21) Appl. No.: 12/668,844

(22) PCT Filed: Jul. 14, 2008

(86) PCT No.: PCT/US2008/069978
§ 371 (c)(1),
(2), (4) Date: Aug. 19, 2010

(87) PCT Pub. No.: WO2009/012222
PCT Pub. Date: Jan. 22, 2009

(65) Prior Publication Data
US 2011/0261354 A1    Oct. 27, 2011

Related U.S. Application Data

(60) Provisional application No. 60/949,725, filed on Jul. 13, 2007, provisional application No. 61/070,735, filed on Mar. 25, 2008.

(51) Int. Cl.
*G01J 3/44*      (2006.01)
*C12M 1/34*      (2006.01)
*G01N 21/64*    (2006.01)
(52) U.S. Cl. .................... 356/301; 435/287.2; 250/203.2
(58) Field of Classification Search .......... 356/300–301, 356/319, 326, 328, 73; 600/473, 476; 378/37; 435/287.2; 250/203.2, 201.3
See application file for complete search history.

(56) References Cited

U.S. PATENT DOCUMENTS

| | | | |
|---|---|---|---|
| 4,008,961 A | | 2/1977 | Barrett |
| 4,068,953 A | | 1/1978 | Harney et al. |
| 4,620,284 A | * | 10/1986 | Schnell et al. .................. 702/28 |
| 5,153,670 A | * | 10/1992 | Jannson et al. ............... 356/301 |
| 5,272,332 A | * | 12/1993 | Ning ............................. 250/226 |
| 5,275,168 A | | 1/1994 | Reinjes et al. |

(Continued)

FOREIGN PATENT DOCUMENTS

WO     2005059526 A1    6/2005

(Continued)

OTHER PUBLICATIONS

PCT/US2008/069978, Search Report & Written Opinion, mailed Sep. 25, 2008.

(Continued)

*Primary Examiner* — Sang Nguyen
(74) *Attorney, Agent, or Firm* — John V. Daniluck; Cedric A. D'Hue; Bingham Greenebaum Doll LLP

(57) ABSTRACT

System, method, and apparatus for determining the composition of a sample of material. In one embodiment, the method pertains to the counting of photons that were inelastically scattered by the sample, and for minimizing the effects of fluorescent or phosphorescent photons. In yet another embodiment of the invention, a sample is illuminated by a repetitive pulse of monochromatic light, and the resultant scattered photons from the samples are collected and counted during a predetermined integration period. Yet other embodiments pertain to a low-cost, computer-controlled system for repetitively counting inelastically scattered photons so as to create a Raman histogram and a Raman spectrogram of the photons.

29 Claims, 36 Drawing Sheets

U.S. PATENT DOCUMENTS

| | | |
|---|---|---|
| 5,673,109 A * | 9/1997 | Keilbach .................. 356/301 |
| 5,807,261 A * | 9/1998 | Benaron et al. ............ 600/473 |
| 6,326,910 B1 | 12/2001 | Hayduk et al. |
| 6,571,118 B1 | 5/2003 | Utzinger et al. |
| 6,642,495 B2 | 11/2003 | Lowrance et al. |
| 6,748,259 B1 | 6/2004 | Benaron et al. |
| 6,915,955 B2 | 7/2005 | Jung et al. |
| 7,116,416 B1 | 10/2006 | Boss et al. |
| 7,362,426 B1 | 4/2008 | Yoo |
| 7,362,431 B2 | 4/2008 | Leona |
| 7,498,551 B2 * | 3/2009 | Werner et al. ............ 250/203.2 |
| 8,072,595 B1 * | 12/2011 | Bastiaans et al. ........... 356/301 |
| 8,094,294 B2 * | 1/2012 | Treado et al. ................ 356/73 |
| 2003/0120137 A1 * | 6/2003 | Pawluczyk ................ 600/310 |
| 2004/0042006 A1 | 3/2004 | Chen et al. |
| 2004/0145735 A1 | 7/2004 | Silberbert et al. |
| 2007/0013908 A1 | 1/2007 | Lett et al. |
| 2007/0156320 A1 | 7/2007 | Breed et al. |
| 2007/0222982 A1 | 9/2007 | Tuschel et al. |
| 2007/0285658 A1 | 12/2007 | Claps et al. |
| 2008/0018890 A1 | 1/2008 | Maity et al. |
| 2008/0085550 A1 * | 4/2008 | Werner et al. ............. 435/287.2 |
| 2008/0117416 A1 | 5/2008 | Hunter et al. |
| 2009/0097020 A1 * | 4/2009 | Treado et al. ................ 356/301 |
| 2009/0238333 A1 * | 9/2009 | Matousek et al. ............ 378/37 |

FOREIGN PATENT DOCUMENTS

| | | |
|---|---|---|
| WO | 2008016927 A1 | 2/2008 |

OTHER PUBLICATIONS

PCT/US2008/069978, Response to Written Opinion, filed Apr. 14, 2009.

* cited by examiner

PMT output signal properties     Signal amplification & filtering

(a)                                    (b)

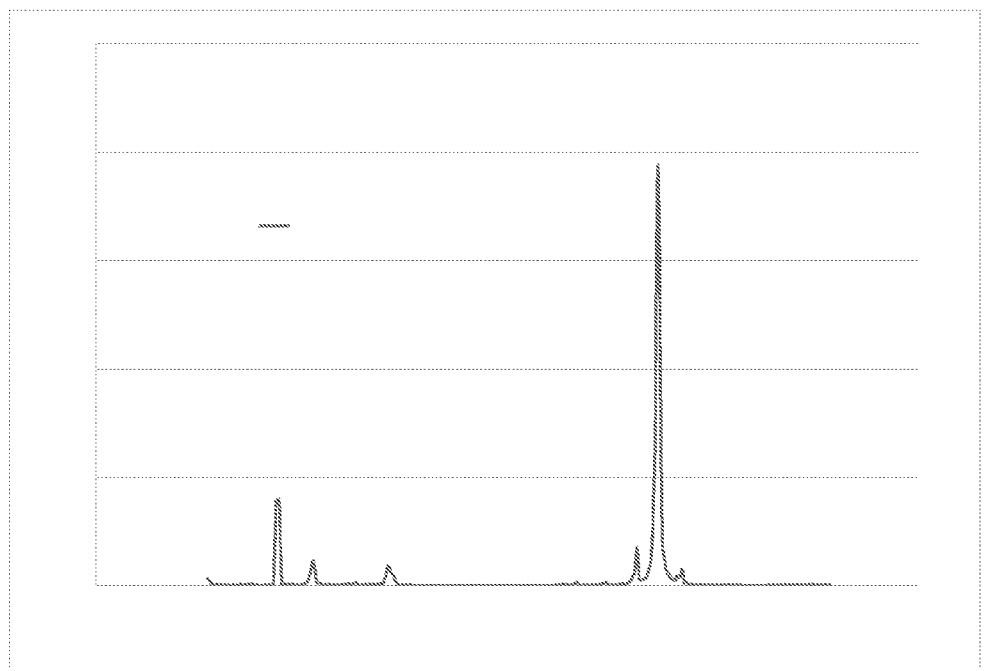
FIG. 10.1a

Benzene (C$_6$H$_6$) CW Raman only signature at 532nm excitation (a)

Benzene (C$_6$H$_6$) CW Raman + RhB signature at 532nm excitation (b)

(a)

(b)

| Sample | Oil Type | AREA | Gas Chromatography Results (%) | | | | | |
|---|---|---|---|---|---|---|---|---|
| | | | PAL | STE | OLE | LLE | LLN | SATS |
| A | Corn | 1613 | 10.71 | 1.85 | 29.32 | 56.61 | 1.51 | 12.56 |
| | | 1478 | 10.69 | 1.85 | 29.39 | 56.53 | 1.54 | 12.54 |
| B | Canola & Vegetable | 1355 | 4.61 | 2.25 | 60.74 | 22.94 | 9.46 | 6.86 |
| | | 1711 | 4.64 | 2.25 | 60.91 | 22.76 | 9.44 | 6.89 |
| C | Olive | 1643 | 16.54 | 2.7 | 63.88 | 15.76 | 1.12 | 19.24 |
| | | 1909 | 16.6 | 2.71 | 63.86 | 15.76 | 1.07 | 19.31 |
| D | Vegetable | 3063 | 10.59 | 4.23 | 22.98 | 54.51 | 7.69 | 14.82 |
| | | 2929 | 10.56 | 4.26 | 23 | 54.51 | 7.66 | 14.82 |
| E | Sunflower | 2487 | 4.61 | 3.98 | 62.56 | 27.33 | 1.52 | 8.59 |
| | | 1812 | 4.63 | 4.25 | 62.8 | 27.85 | 0.46 | 8.86 |
| F | Canola | 2196 | 4.17 | 1.99 | 63.64 | 20.15 | 10.06 | 6.16 |
| | | 2175 | 4.15 | 2.03 | 63.58 | 20.17 | 10.07 | 6.18 |
| G | Olive | 1806 | 15.95 | 2.83 | 63.74 | 16.51 | 0.97 | 18.78 |
| | | 2362 | 15.97 | 2.84 | 63.99 | 16.32 | 0.89 | 18.81 |
| H | Canola, Soy, & Olive | 2512 | 5.94 | 2.67 | 54.99 | 28.06 | 8.34 | 8.61 |
| | | 2327 | 5.9 | 2.66 | 54.97 | 28.06 | 8.42 | 8.56 |
| I | Sesame Seed | 2653 | 9.71 | 5.54 | 39.33 | 44.8 | 0.63 | 15.25 |
| | | 1065 | 9.77 | 5.48 | 39.5 | 44.67 | 0.58 | 15.25 |
| J | Canola | 2330 | 4.48 | 2.03 | 62.51 | 21.02 | 9.96 | 6.51 |
| | | 2751 | 4.41 | 2.04 | 62.46 | 21.07 | 10.02 | 6.45 |
| K | Safflower | 2062 | 6.9 | 2.6 | 15.68 | 73.94 | 0.88 | 9.5 |
| | | 2868 | 6.93 | 2.63 | 15.21 | 74.46 | 0.76 | 9.56 |
| L | Olive | 2190 | 17.88 | 2.7 | 59.92 | 18.62 | 0.89 | 20.58 |
| | | 2370 | 17.87 | 2.68 | 60.15 | 18.34 | 0.95 | 20.55 |
| M | Canola | 2538 | 4.23 | 2.14 | 65.54 | 19.51 | 8.59 | 6.37 |
| | | 2917 | 4.24 | 2.14 | 65.84 | 19.17 | 8.61 | 6.38 |
| N | Peanut | 2193 | 10.1 | 2.51 | 55.07 | 30.03 | 2.28 | 12.61 |
| | | 2106 | 10.12 | 2.52 | 55.11 | 30.06 | 2.19 | 12.64 |
| O | Olive | 2838 | 16.28 | 2.8 | 63.62 | 16.42 | 0.88 | 19.08 |
| | | 2277 | 16.24 | 2.79 | 63.29 | 16.69 | 1.00 | 19.03 |
| P | Vegetable | 2225 | 10.61 | 4.07 | 24.38 | 52.84 | 8.09 | 14.68 |
| | | 3130 | 10.67 | 4.09 | 24.11 | 53.05 | 8.08 | 14.76 |
| Q | Soy & Canola | 2118 | 5.39 | 0.07 | 2.33 | 64.73 | 27.48 | 5.46 |
| | | 2682 | 5.34 | 0.07 | 2.34 | 65.89 | 26.35 | 5.41 |
| R | Flaxseed | 1764 | 5.4 | 3.67 | 17.28 | 16.09 | 57.56 | 9.07 |
| | | 1537 | 5.33 | 3.69 | 16.63 | 16.07 | 58.27 | 9.02 |
| S | Olive Oil | 1574 | 10.96 | 3.52 | 78.14 | 5.8 | 1.59 | 14.48 |
| | | 1676 | 10.98 | 3.52 | 78.54 | 5.75 | 1.21 | 14.5 |
| T | Grapeseed | 2007 | 7.44 | 4.04 | 20.56 | 67.13 | 0.83 | 11.48 |
| | | 1870 | 7.39 | 4.06 | 19.87 | 67.58 | 1.09 | 11.45 |
| U | Sunflower | 2790 | 4.84 | 3.73 | 59.52 | 31.23 | 0.69 | 8.57 |
| | | 1661 | 4.85 | 3.7 | 59.3 | 31.59 | 0.55 | 8.55 |
| V | Coconut | 186 | 33.89 | 10.35 | 39.68 | 14.95 | 1.13 | 44.24 |
| | | 187 | 36.13 | 10.9 | 33.51 | 18.01 | 1.45 | 47.03 |
| W | Palm | 688 | 38.37 | 5.21 | 44.72 | 11.13 | 0.58 | 43.58 |
| | | 943 | 38.18 | 5.21 | 45.44 | 10.62 | 0.55 | 43.39 |

Table prepared by DICKEY-john Corporation
Tests performed on behalf of DICKEY-john at Iowa State University PAL = Palmitic
STE = Stearic
OLE = Oleic
LLE = Linoleic
LLN = Linolenic
SATS = Saturates (PAL + STE)

FIG. 41

TIME RESOLVED RAMAN SPECTROSCOPY

CROSS REFERENCE TO RELATED APPLICATIONS

This application is a national stage application of PCT Application No. PCT/US08/69978, filed Jul. 14, 2008, which claims the benefit of priority to U.S. Provisional Patent Application Ser. No. 60/949,725, filed Jul. 13, 2007 and to U.S. Provisional Patent Application No. 61/070,735, filed Mar. 25, 2008, all of which are incorporated herein by reference.

FIELD OF THE INVENTION

The inventions described herein relate to measurement and analysis of radiation emitted from a substance, and in particular to time-based techniques for analysis of a spectrum of a substance.

BACKGROUND OF THE INVENTION

Raman spectroscopy is a photon scattering phenomenon. In this technique a laser is directed toward a test specimen and photon-molecule collisions are observed. The amount of energy transferred in the collision corresponds to the vibrational and rotational energy states of the target molecule bonds. The spectrum of observed scattered frequencies, known as the Raman spectrum, enables distinction of compounds containing the same atoms as long as they exist in different multiples or in different bond combinations. In general, the Raman line intensities relate to bonds in a molecule and will be consistent with molecule stoichiometry.

Recently interest has renewed in the identification and quantification of various oil compounds in common foods. It is known that the presence of unsaturated fatty acids such as oleic, linoleic and linolenic acid in food can help to lower total Low-Density Lipoprotein (LDL) cholesterol in the blood. Hence their presence in foods is encouraged, particularly as alternatives to saturated fats which are linked with obesity, heart diseases and their accompanying adverse effects in humans. Traditional means to detect these compounds are limited to methods such as gas chromatography/mass spectrometry (GC/MS) and NIR reflectance, but GC/MS analysis typically involves rather cumbersome sample gathering and preparation and NIR analysis tends to lack the sensitivity that the market may demand to differentiate substances containing minor variations in the target fatty acids. It is therefore believed that alternative analysis techniques may warrant pursuit. The work contained herein explores the use of an alternative method to identify and quantify these compounds which involves the use of time-resolved Raman spectroscopy. Further, this work is equally applicable to situations in which both the Raman and fluorescence information from a sample is to be gathered.

SUMMARY OF THE INVENTION

One aspect of the present invention pertains to a system for acquiring a Raman spectrum from a sample. In one embodiment, the system is a low cost system with high resolution and high sensitivity. In one embodiment, the system includes a computer-controlled monochromator and a photo-multiplier tube, resulting in an accurate system that is much less expensive than current laboratory systems.

Yet another aspect of the present invention pertains to the ability to observe and measure both Raman-scattered photons as well as fluorescence or phosphorescence signatures with a single instrument. In some embodiments, there is a short period of integration during which the inelastically scattered photons are collected, corresponding to the Raman spectrum. In yet another embodiment there is a longer period of integration in which both Raman and fluorescence photons are measured.

Yet another aspect of the invention pertains to inducing a Raman signature in the range of about 500 nm to about 600 nm. By limiting the spectrum in this manner, there is less chance of damaging the sample either through electronic excitations (such as with UV excitation), or by heating the sample (such as with IR source).

The present invention pertains to methods for determining the composition of a sample. One aspect pertains to providing a source of monochromatic pulsed light (for example, a laser, a filtered LED, or other filtered light source, whether coherent or incoherent) and a sensor for counting individual photons. Another aspect includes illuminating the sample with a pulse of light having a beginning and an ending, wherein some of the source photons are scattered by the sample. Still further aspects of the invention include collecting the scattered photons and counting the inelastically scattered photons with a sensor during a predetermined period of time, the period starting proximate to the pulse; and stopping said counting before collecting a statistically significant sample of photons resulting from fluorescence, phosphorescence, or any other form of excited state emission caused by the pulsed light source.

Another embodiment of the present invention pertains to an apparatus for determining the composition of a sample. One aspect of the present invention includes a repetitive source of pulsed light, a chamber for receiving the sample and a probe for directing the pulsed light onto the sample and collecting the photons scattered by the sample. Further aspects of the present invention include a controllable filter for receiving the collected photons and substantially eliminating photons not within a selectable frequency band defined between a first selectable lower frequency and a second selectable higher frequency.

Yet other embodiments of the present invention include a photon counting sensor for receiving the photons from a monochromator (such as a filter, Bragg grating, holographic gratings, and related devices) and providing a count signal corresponding to the number of photons within the frequency band within a specified time; and a controller having a plurality of memory bins and being operably connected to a source, a filter, and a sensor. Other aspects of the present invention pertain to a controller receiving the count signal from a first pulse, storing the count signal as a first count signal in a first memory bin associated with the first frequency band, the controller further selecting a different frequency band for filtering a subsequent pulse from a source.

Yet another aspect of the present invention pertains to a spectrometer incorporating a photo-multiplier tube, a charge coupled device (CCD), avalanche photodiode, or other detectors that can count individual photons being scattered inelastically from the sample.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these myriad combinations is excessive and unnecessary.

These are various other aspects of the present inventions will be shown in the text, figures, and claims that follow.

DESCRIPTION OF THE DRAWINGS

FIG. 10.1a: Time-resolved Raman signature of neat benzene as measured by a measurement system according to one embodiment of the present invention.

FIG. 41: Evaluation of various oil samples showing gas chromatograph results.

DESCRIPTION OF THE PREFERRED EMBODIMENT

Figure 1:
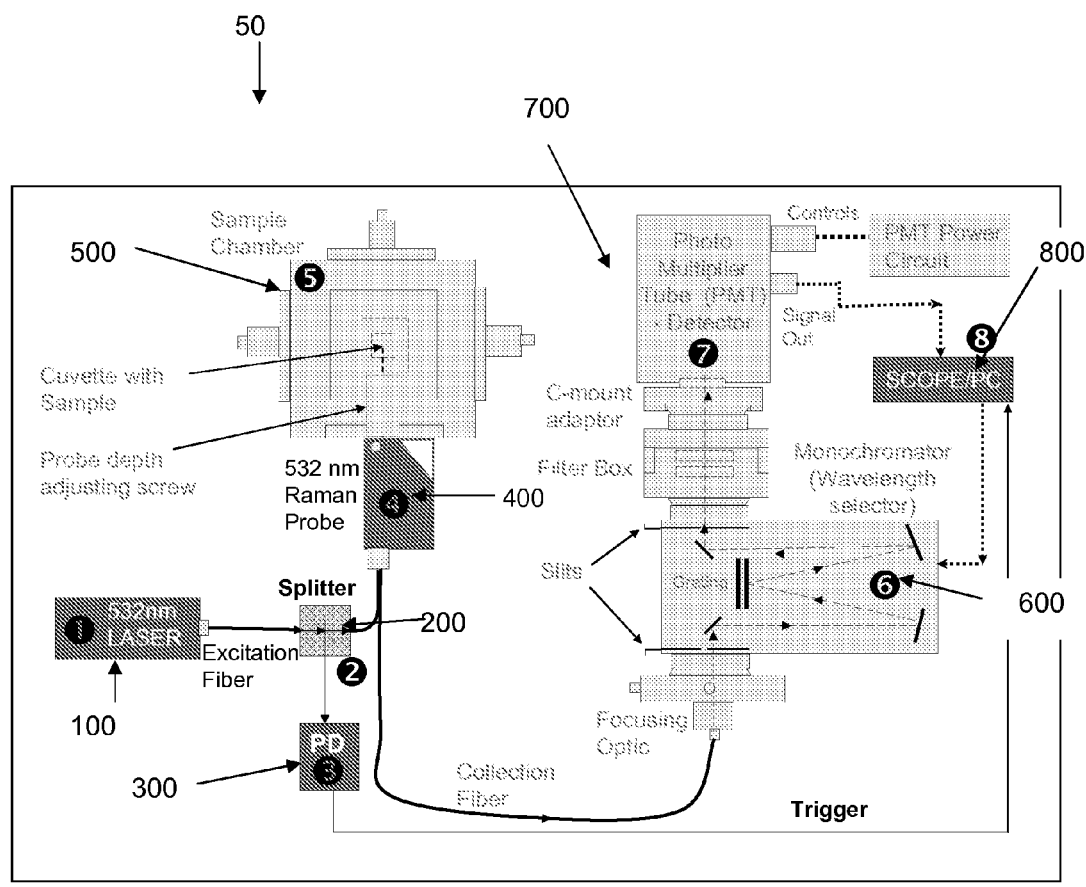
FIG. 1: A system for time-resolved (TR) Raman spectroscopy according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The following description includes certain specific wavelengths, frequencies, weights, times, voltages, dimensions, and other quantities. It is understood that the specific values given are illustrative only, and that the many embodiments of the inventions described herein are not so limited.

When a stream of photons collides with matter, various events can occur, depending primarily on the energy content of the photons (their frequency) and on the physical properties of matter. Depending on the cross-section presented by the matter to the incoming photons, interaction can take on several forms: photons can be completely transmitted through the sample without any interchange of energy between the matter and the photons (commonly occurs in samples appearing transparent to the incoming frequency of light), photons can be completely elastically scattered or reflected back without exchange of energy (commonly known as Rayleigh scattering, occurs in opaque objects, mirrors or gratings) or interaction can occur with various degrees of energy exchange.

In the case of energy exchange, two phenomena are possible, depending on whether the photons interact with single atoms or with molecular bonds between atoms: inelastic scattering of photons or their complete absorption by the atom.

If case of inelastic scattering, a bond between two atoms can be treated as a classical harmonic oscillator where the bond is the spring and the atoms are the two masses at the end of the spring. In the case of the classical harmonic oscillator, depending on the weight of the masses and the spring constant of the spring, this system will oscillate at a certain resonant energy when some energy is imparted upon it. Similarly, two atoms have mass and there is a certain bond energy associated with the two, making the system oscillate at a particular resonant frequency when excited. The bond between the two atoms is associated with only certain resonant energies, and these values will be different for every combination of atoms. Vibrations and rotations that actually occur are dependant on the bond geometry and on the number of degrees of freedom a particular molecule exhibits. A good resource on the complete theoretical treatment on this matter along with theoretical predictions of resonant energies for every bond is a Raman spectroscopy book by Long, 1976 as well as Nakamoto, 1976.

When photons collide with a molecule, only a particular amount of energy will be transferred from the photons to the bonds inside this molecule because these bonds can only resonate at particular frequencies, thus absorbing only a predetermined amount of energy necessary for these resonant vibrations and/or rotations. As a result of this, incoming photons that are scattered are reduced in energy from their initial state by $\Delta\lambda = \lambda_f - \lambda_i$. This reduction in energy decreases the frequency (and increases wavelength) of scattered photons compared to the incoming photons of the excitation source. Since these energy transfers are particular to every bond type, measuring the intensity of scattered light as a function of energy shift from the excitation source will create a spectrum where peaks in intensity will appear at each energy shift particular to the bond causing the scattering. Since different atoms create different bonds with different resonant frequencies, these energy shifts will be particular to every bond and can be used as a signature to describe every chemical bond found in a particular sample.

While this reduction of a photon's energy is known as Stokes shift and is by far a more common phenomenon, it is also possible that an already excited bond transfers a specific amount of energy to the incoming photon, thereby increasing its energy and causing a shift towards higher frequencies of light instead to lower ones. This is known as an anti-Stokes shift and while not seen as commonly, is also very specific of the bond structure involved.

This scattering associated with the inelastic collision of photons with matter was named Raman scattering after Indian scientist Sir Chandrasekhara Venkata Raman who discovered this phenomenon and was awarded a Nobel Prize for his work in 1930. He experimented with sunlight, by passing it through a photographic filter to create a monochromatic source (lasers are used today) and noted that a changed frequency of scattered light emanated from a sample exposed to the monochromatic light source.

A second phenomenon that can occur in the same frequency range in nearly the same time as Raman scattering is fluorescence emission. To understand the difference between the two phenomena, Bohr's standard model of the atom must be considered where a single atom has various energy levels where its surrounding electrons can reside. Following the particle-wave duality of light theory, photons can behave like particles in the sense that collisions with atoms carry a certain probability and the energy of the photons can be completely transferred to the outer most electrons which, behaving like waves, can jump to an excited state or level of higher energy. This energy can be dissipated through various mechanisms, where electrons fall back down to a lower and more stable energy level, releasing either light or heat, depending on the atom. In this phenomenon, known as fluorescence, some of this energy can be observed in the visible part of the spectrum. This phenomenon can occur only if the incident photons had enough energy to excite the electrons by the whole (quantized) energy level. Further, sample atoms have to be susceptible to absorption at the frequency of the excitation photons.

Like Raman photons, fluorescent photons will be shifted in energy from the excitation source, but will only do so towards less energy (longer wavelength) and never higher like in the case of anti-Stokes Raman shifts. This is true because an excited atom will never be able to transfer "only a little bit" of energy to an already existing incoming photon; an electron must fall into the lower energy state and this is equivalent to one quanta of energy which will produce one whole new quanta of light (a photon). This explains why the incoming and newly created photons are different in energy (and thus wavelength).

One difference between Raman and fluorescence is that (Stokes-shift) Raman involves an increase in the vibrational energy of the bond of atoms, while fluorescence is an emission due to the actual absorption of the photons into a single atom. Further, fluorescence occurs later in time compared to Raman because it takes less time for the photons to inelastically scatter than to be first absorbed by the atom and then reemitted again. Depending on the excitation frequency, certain atoms may or may not fluoresce, while every bond will have a resonant vibrational energy and thus every bond will have a Raman signature but not every bond will have fluorescence signature. Finally, Raman signatures are very narrow and highly bond-specific while fluorescence has a broad wavelength spread, indicating that only certain "types" of atoms are present in the sample but not specifically what bond structures these atoms may form in the sample. Fluorescence intensity can be linked to concentration of certain solute in a solution, but not to concentration of a particular bond type.

If a continuous wave laser is used as an excitation source (meaning the laser emission is continuously turned on), both Raman and possibly fluorescence phenomena occur continuously in time, and for some samples the probability of fluorescence emissions is orders of magnitude higher than for Raman photon scattering. Samples that fluoresce will then completely vanquish the Raman signal to noise ratio (noise being undesirable fluorescence, as well as other forms of electrical and optical interference) because in a non-time resolved case, both Raman and (much more dominant) fluorescence photons look exactly alike to the detector.

Various methods exist to combat fluorescence problems: switching to a longer wavelength excitation that is less energetic and causes less fluorescence—but usually less Raman as well due to the fact that optical cross-section for Raman $\sim 1/\lambda^4$; shifted excitation Raman difference spectroscopy (SERDS), relying on the fact that two Raman signatures obtained by two excitation sources shifted from each other by a small amount (<2 nm) will be also shifted by a similar amount while the broadband fluorescence profile will look the same despite the shift in excitation, so taking the difference of these two spectra would remove the effect of fluorescence and reveal much stronger Raman peaks.

A thought experiment can be conducted with only two photons leaving the source at the same time and one causes a fluorescent photon to be emitted while the other one causes a Raman photon to be scattered. It is known from theoretical calculations and observations that the Raman photon will always arrive at the detector before the fluorescent one. This time difference varies from sample to sample, but Raman photons occur only picoseconds after the initial excitation; fluorescence photons can take anywhere from 1 ns~1 ms, implying a considerable temporal separation between the two phenomena. This is due to the fact that Raman photons can only be scattered while the source is on (Raman transition takes only a picosecond or less (Giorgini et al, 2006)), while fluorescent photons occur because of the energy stored in the excited electron states (this process typically requires more than a nanosecond). This energy is subsequently released in form of a photon, which depending on the atom can occur considerably later time after the source has been turned off.

Figure 20:
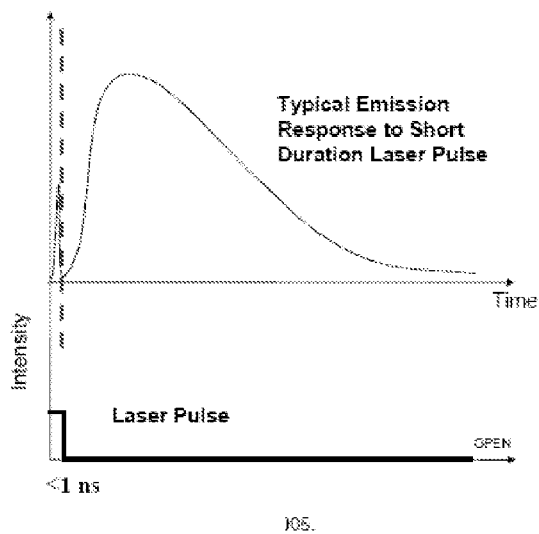
FIG. 20: Improvement of SNR using temporal separation of Raman peaks from fluorescence peaks.

Therefore, if a source having a reasonably short pulse duration is used (In one embodiment, less than about 0.5 ns), it is possible in some chemical systems to discriminate between Raman photons that come first and fluorescent ones that come later in time after this pulse. In another embodiment of the present invention, a wider pulse laser can also be used, but then the scattered photons need be time-gated and observed only during the first ns or less of the duration of the laser pulse—before the fluorescing and phosphorescing photons have had time to be emitted. Such a method would be called a time-resolved case where fluorescence is rejected by counting only the photons that occur in a certain early time interval before the fluorescent ones start appearing in significant quantities. This method is graphically showed in the time domain in FIG. 20.

Much longer laser pulses approach the continuous wave case where photons from the beginning of the laser pulse start inducing fluorescence before the detector had an opportunity to measure the Raman photons due to the excitation photons from the end of the laser pulse, thus convoluting the two phenomena and reducing the SNR. Besides pulse width, energy per pulse and laser pulsing frequency also have influence on Raman SNR; due to the low probability of Raman photons scattering, more power in a shorter pulse that occurs at faster repetition rate generally increases the statistical probability of observing Raman photons in a given time interval. Caution must be observed when working with samples with extremely long fluorescence decay times; in a very extreme example where fluorescence lifetime may be on the order of microseconds (as opposed to ns), laser pulsing frequency could not exceed a few hundred kHz, because one laser pulse would overlap in time with fluorescence induced by the previous pulse which would imply that the Raman and fluorescence photons would again be overlapping in time.

Various embodiments of the present invention are directed toward measurement of both the Raman spectrum, as well as the fluorescence or phosphorescence spectrum of a sample. In those embodiments in which it is desired to measure only the Raman spectrum, there is period of integration during which photons inelastically scattered from the sample are counted by a photon-counting sensor. This period of integration is adapted and configured to acquire substantially all the Raman-scattered photons, but not to gather a statistically significant number of fluorescent or phosphorescent-scattered photons. In other embodiments, the integration period can be made substantially longer, in which case both Raman and fluorescent/phosphorescent photons are collected, with the latter signal overwhelming the former signal. In yet other embodiments, the integration period is delayed so as to not begin until after the Raman photons have been collected and delivered to the photon-counting sensor. As one example, this period could be about the same as the width of the light pulse that illuminated the sample, since the Raman signature stops at about the same time as the illumination pulse stops. In yet other embodiments, this delay can be established based on the rise time of the photon-counting sensor or transport lag in the optical and electronic paths (as will be shown later).

By studying Raman spectra obtained for various chemicals, theoretical chemistry calculations of Raman peak locations can be confirmed based on the geometry and chemistry of the bond. Raman peaks found in spectra both acquired using the setup developed in this research as well as from standards found in references in literature can be correlated to particular bonds as predicted by theoretical treatments by Nakamoto, 1976 and Nyquist, 1999. By studying location and amplitude of peaks in the spectrum, chemical composition of the sample can be identified. There is a linear relationship between concentration of solute in the sample and the intensity of Raman peaks, which makes system calibration relatively straightforward.

Most molecular bonds will have a range of Raman frequencies specified although the actual Raman lines (peaks) are fairly narrow. This is due to the fact that bonds between atoms will cause slight shifts in Raman frequency depending on the larger molecular structure around the bond and any physical stretching and bending occurring inside the molecule. Just as the length of the spring (or a string) in a classical oscillator will influence its resonant frequency, bending or stretching of the atomic bonds changes the exact location of Raman peaks. Depending on how one atom is bonded to another, the number of degrees of freedom for the vibrations will be different. An atomic resonator (two atoms and the bond between them) may rotate about bond axis; vibrate along the bond axis or in one of the three spatial dimensions, depending on the freedom of motion based on the other bonds in the same molecule.

The amount of energy transferred in the photon-molecule collision corresponds to the vibrational and rotational energy states of the target molecule bonds. The spectrum of observed scattered frequencies, known as the Raman spectrum, thus relates to the bonds in a molecule and the relative intensity of lines in the spectrum is consistent with molecule stoichiometry. The absolute intensity of the observed scattering phenomenon, termed the Raman cross-section, is proportional to $1/\lambda^4$ (where $\lambda$=wavelength), yet the observed Raman shifts are independent of excitation wavelength since they are a function of the investigated molecule and not the wavelength of incident energy. The specificity of this phenomenon enables distinction of even compounds containing the same atoms as long as they exist in different multiples or in different bond combinations (e.g., while ammonium and nitrate both contain nitrogen, their molecular (or ionic) composition is distinguishable ($NH_4^+$ vs. $NO_3^-$, respectively)).

One embodiment of the present invention includes methods and apparatus to limit the adverse effects of fluorescence and permit Raman analysis in natural settings and involves application of a technique termed time resolved Raman spectroscopy. In this method, a pulsed laser is used to interrogate the test sample. Because Raman is a scattering phenomenon and virtually instantaneous, Raman scattered photons exist during the laser pulse. (See FIG. 20) In contrast, fluorescence, which occurs with a time constant on the order of $10^{-9}$ s, involves the absorption of a photon by atoms within the molecular structure of target compounds and subsequent emission of photons (of typically lower energy) as the atoms at an excited electronic energy state transition back to a ground state. A finite amount of time therefore transpires between incidence and absorption of the excitation photon and emission of the fluorescence photon.

Thus, Raman scattering and fluorescence emissions occur in separate time frames if excited by a non-continuous source of energy. Fluorescence induced by photons associated with the beginning of the laser pulse can start to occur before the laser pulse ends, particularly if the laser pulse is long. The photons emanating from a target sample during the early portion of the laser pulse likely stem from Raman scattering rather than fluorescence with statistical significance, facilitating a marked improvement in the Raman signal-to-noise ratio (SNR) in the presence of a fluorophore relative to that achievable with a continuous wave (CW) (non-pulsed) system. While time-resolved "separation" of Raman from fluorescence has been previously demonstrated in laboratory research settings (Yaney, 1972; Harris et. al., 1976; Burgess and Shepherd, 1977; Kamogawa, et. al., 1998; Everall et. al., 2001), until recently the equipment and methods needed for this approach has been largely impractical.

Figure 21A:
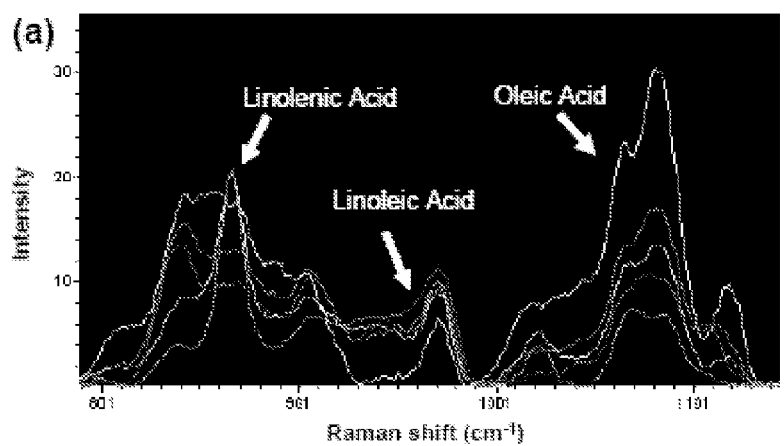
FIG. 21: Applicability of PLS analysis to (a) Raman signatures of fatty acids, and (b) correlation between Raman test results and GC-MS analyses.
Figure 21B:
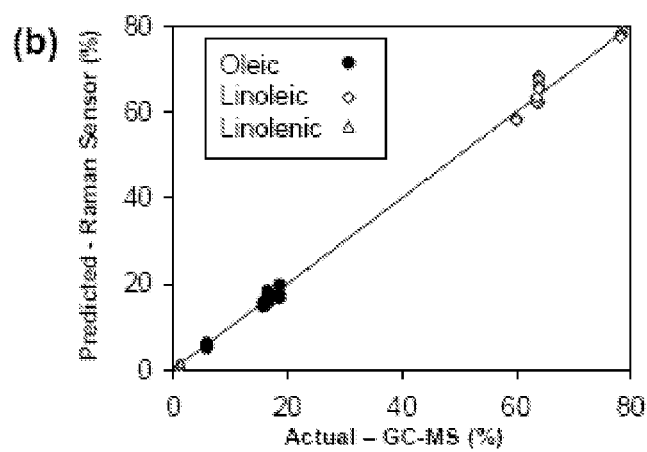
Figure 22A:
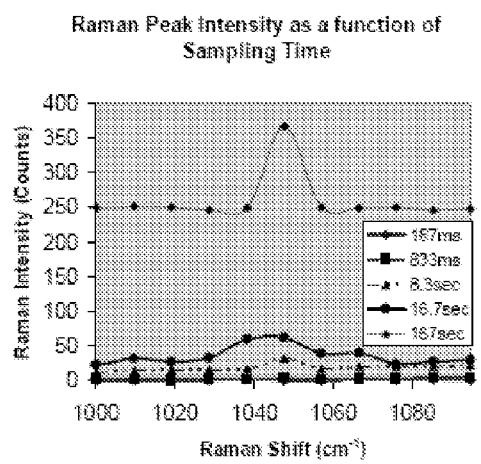
FIG. 22: Nitrate peak improvement with increasing sampling time in TR mode.
Figure 22B:
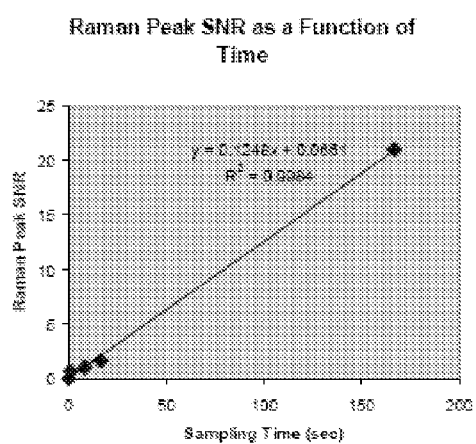

The range of energy associated with any given vibrational mode of a molecule (which is directly related to the bandwidth of the Raman line) is inherently narrow, which can often allow ready distinction of compounds present in mixtures. In very complex systems (as will likely be encountered in the geoenvironment), there is the potential for Raman bands to overlap, partially or completely. However, Raman intensities are also tied to molecular stoichiometry, and thus the signatures of mixtures are a superposition of the signatures of the mixture constituents. While not always straightforward to decouple, multiple researchers have successfully applied partial least squares or principal component analysis to quantitatively assess constituents in multi-compound solutions (e.g., Cooper et. al., 1995; Goetz et. al. 1995; Afseth et. al., 2005, Oshima, et. al., 2006). One embodiment of the present invention has been used to quantify the presence of oleic, linoleic, and linolenic fatty acids in vegetable oils despite the clear overlap of the fundamental Raman signatures of these acids, and evidence of fluorescence from several know fluorophores under 532 nm excitation, namely tocopherol (vitamin E), chlorophyll and phenolic antioxidants (Poulli et. al., 2005). FIG. 21(a) presents the overlapping Raman signatures of the individual acids (Lambda Solutions, 2005), and FIG. 21(b) illustrates the correlation between Raman observations of olive oil samples at select Raman lines of interest and concentrations of the individual fatty acids those samples obtained via GC-MS tests performed on the same samples.

By operating in a photon counting mode, with a selective voltage count threshold, and at kHz repetition rates, a system according to one embodiment of the present invention has sensitivity and potential to rapidly acquire high SNR Raman signatures even at field relevant concentrations. Since photon counting is effectively a "digital" process—count=1, no count=0—increases in sampling time provide an opportunity to capture photons from even low concentration samples while effectively rejecting noise from both electrical interference and stray light. In preliminary tests, a linear correlation has been observed between the concentration of $NO_3$_N in aqueous solutions of $NH_4NO_3$ and the intensity of the N—O Raman line at 1041 $cm^{-1}$ down to ppm level concentrations with a sampling time of about two minutes. Since the "noise" floor in photon counting is governed primarily by the variance of the PMT dark count, there are ample opportunities to improve the SNR (and detection limits) by optimizing sampling time (to a limit), reducing laser power losses in the system, boosting photon collection efficiency in the test cell, and to some extent improving detection circuitry. When monitoring geoenvironmental processes, sampling time is typically a readily adjusted variable.

Figure 39:
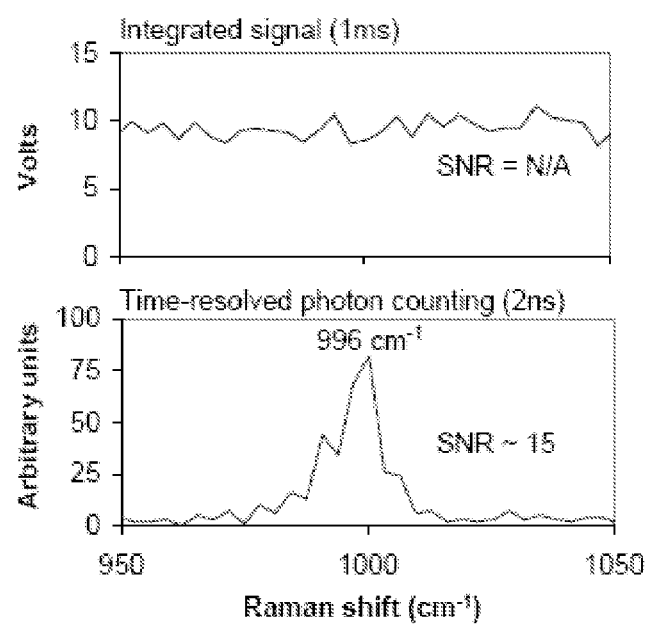
FIG. 39: A comparison of continuous wave (integrated) and time resolved measurements of benzene.

Due to the short pulse excitation source and GHz time gating data acquisition circuitry, Raman signals can be acquired with statistical significance in a time interval prior to the onset of significant fluorescence emission and without deconvolution algorithms. To illustrate this point one embodiment of the present invention was used in experiments on a solution consisting of neat benzene doped with rhodamine B (a known fluorophore under 532 nm excitation, with a fluorescence lifetime of approximately 1.7 ns—notably shorter than almost any compound likely to be encountered in an environmental setting). FIG. 39 contrasts the Raman signature of the 996 $cm^{-1}$ benzene line under CW conditions (top) in which the response is composed of the integrated PMT signal over approximately 1 ms, with the signal obtained via photon counting in a 2 ns window of time after initiation of pulsed laser excitation and before onset of significant fluorescence (bottom). In this experiment there is no indication of the benzene Raman line in the CW case yet the system achieves an SNR of ~15 at the 996 $cm^{-1}$ Raman line when the same sample is analyzed using the prototype time-resolved Raman system operating in photon counting mode.

By operating the pulsed source of light at wavelengths greater than about 500 nm and less than about 600 nm (and in one embodiment, 532 nm) in the visible range of the optical spectrum, one embodiment of the present balances the tradeoffs that must be made between Raman signal intensity and peak resolution while limiting the potential to cause fluorescence in many compounds. This provides two aspects: (1) enhanced Raman cross-section, and (2) improved Raman peak resolution in complex samples.

Operating at 500-600 nm, system 500 offers a 16-fold and 4.7-fold advantage in Raman signal intensity over 1064 nm and 785 nm systems (traditionally used to limit fluorescence), respectively, due to the $1/\lambda^4$ dependence of the Raman cross section, revealing features of low concentration constituents not prevalent in traditional infra-red analyses. Some shift toward the UV could provide preferable signal intensity without excessive fluorescence.

Use of a 500-600 nm source permits resolution of Raman peaks separated by as little as 17 $cm^{-1}$ using low cost 0.5 nm resolution spectrometers (vs~70 $cm^{-1}$ using deep UV). With increasing sample complexity (i.e., solutions containing multiple unknowns), more Raman peaks will be present and this yields deeper compositional insight at low cost.

Systems 150 and 50 also provide a foundation for a fieldable distributed sensing system based a fieldable system 120 includes fiber-coupled components. In one embodiment, the present invention contemplates a measurement system that is adapted and configured to be portable. The components shown and described herein are packaged for field research, including provisions for powering the measurement system with a battery or other form of portable power supply.

The fiber coupled design of the sensor provides great flexibility in the location and design of test points for a field monitoring system. With incorporation of an optical switch, the sensing unit can be configured to observe multiple points in wells, horizontal borings, or other in-situ locations to provide rich insight into the movement of source zone contaminants or the related migration of contaminant plumes.

A fieldable system 150 or 50 further permits non-contact assessment: Since Raman spectroscopy makes use of a focused laser source there is the potential to evaluate target compounds through a protective optically transparent window, facilitating the development of a robust monitoring system that can be effectively protected from the elements while in service in the field, whether buried in the ground or immersed in water.

System 150 or 50 makes use of custom and commercially available elements and, is nearly an order of magnitude less expensive than comparable traditional instruments. In addition, the fiber-coupled system design offers the potential to reduce overall monitoring costs by sharing a single laser source, optical monochromator, and detection electronics unit to monitor multiple points in the environment using optical switching hardware now prevalent in the telecommunications industry to connect this hardware to a network of test points.

According to one embodiment of the present invention, there is a time resolved Raman spectroscopy system 50 using a pulsed 532 nm laser 100, a PMT detector 300 and ultra-fast sampling electronics 700, 800 (see FIG. 1). This system calibrated linearly, and in one embodiment reached a detection limit of 30 ppm for nitrate in aqueous solution and showed promise of further SNR and detection limit improvement through increase in sampling time and optimization of the time resolved methods. SNR improvement is approximately linearly proportional to the increase in sampling time with a ratio of 1:1.

Figure 40:
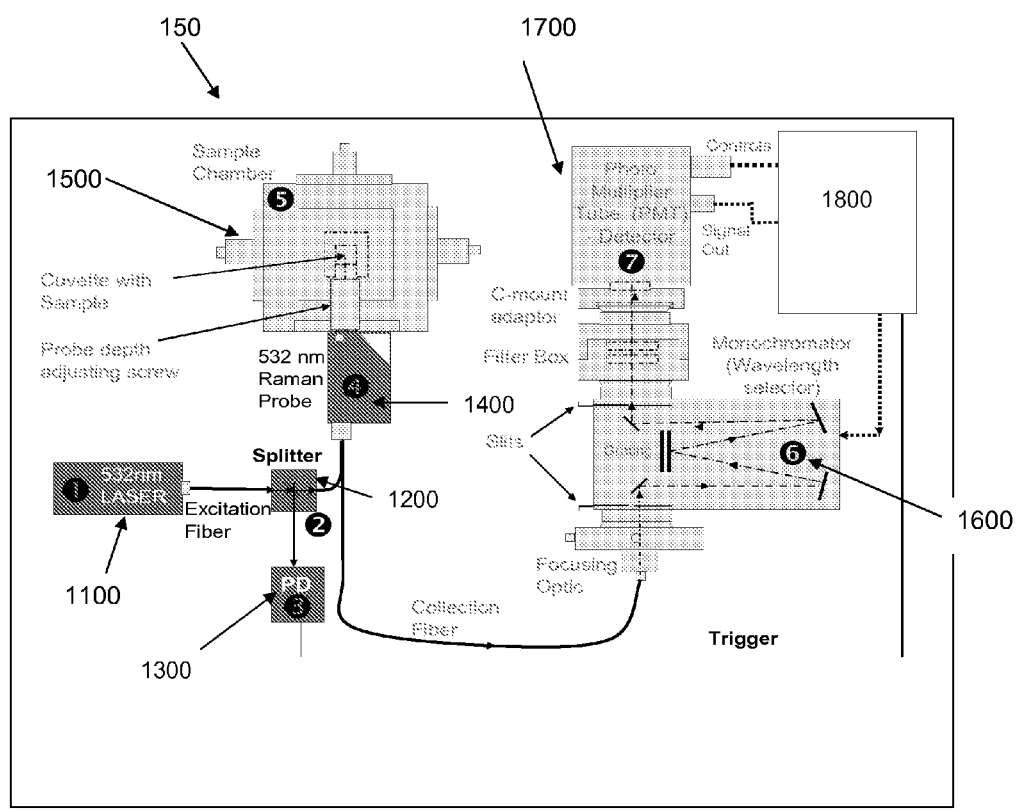
FIG. 40: A Raman spectrometric system according to another embodiment of the present invention.

Yet another embodiment of the present invention is shown in FIG. 40. System 150 of FIG. 40 is similar to system 50, except that system 150 includes a computer controller 100 that is operably connected to photo-multiplier 1700, monochromator 1600, and photodiode 1300. Computer controller 1800 receives a count signal from PMT 700, and further controls the functions of PMT 1700. Controller 1800 includes a plurality of memory bins (which will be described later) that store data corresponding to the count signal provided by PMT 1700. Further, controller 1800 preferably controls the band of monochromator 1600 through which returned, scattered photons are filtered. Preferably, controller 1800 receives a triggering signal from photodiode 1300 and uses this triggering signal to establish a period of integration during which the counted signal from PMT 1700 is acquired and placed in memory. In the descriptions that follow, the various system components are further described with regards to both systems 50 and 150.

Figure 10A:
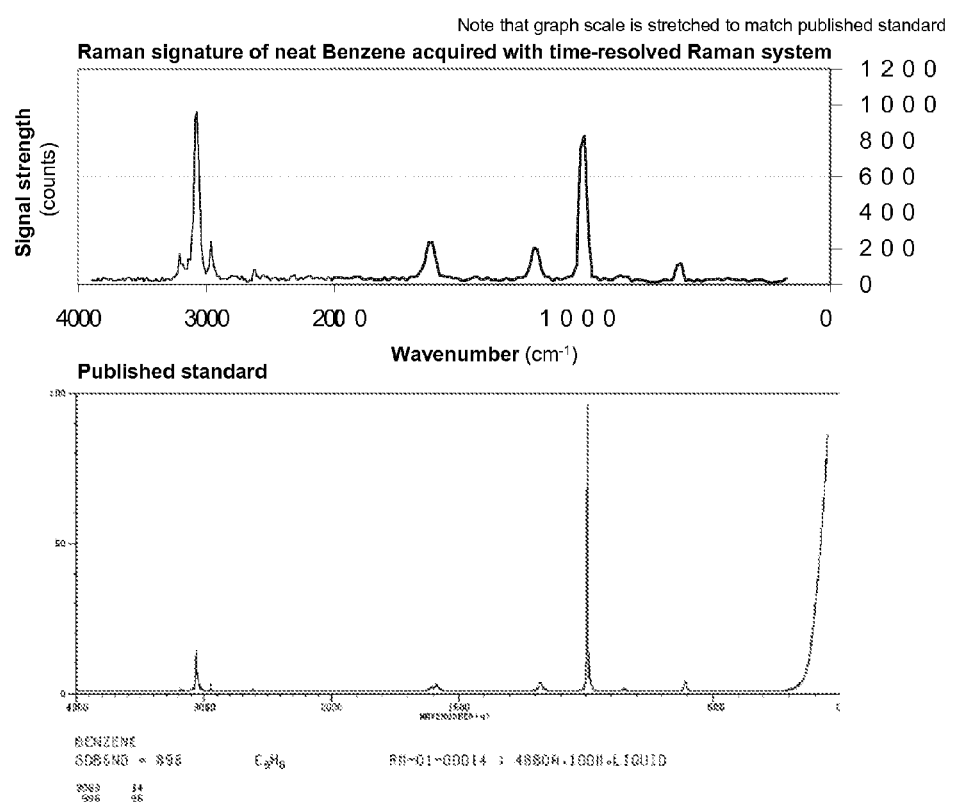
FIG. 10a: Time-resolved Raman signature of neat benzene—comparison of response according to one measurement system of the present invention to published standards.
Figure 10B:
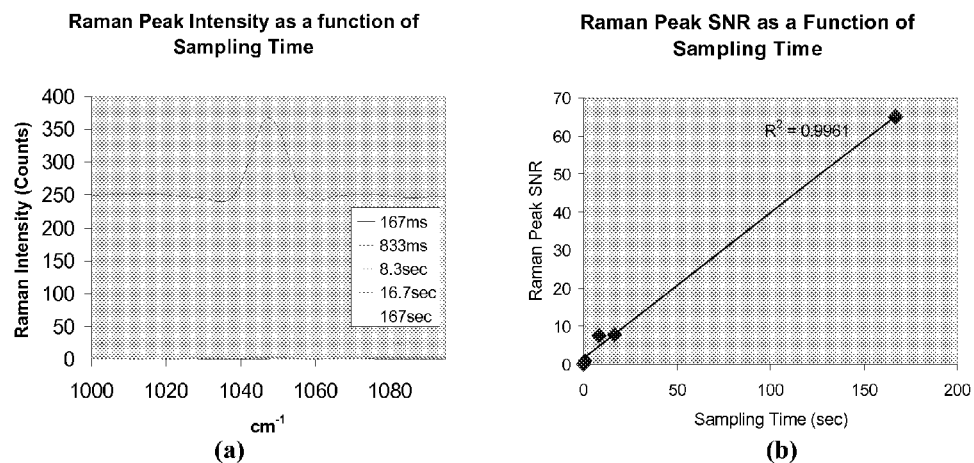
FIG. 10b: Nitrate peak improvement with increasing sampling time in TR mode.

The ability of the time resolved system 50 to distinguish Raman scattered photons amidst fluorescence was demonstrated successfully on Rhodamine B doped benzene (see FIG. 10*b*). The benzene Raman peak was resolved by optimizing the location and size of the sampling window in time (window characteristics: width about 2.3 ns, start time defined by the earliest photon scattering arrival at PMT 700). An increase in SNR from 1 to 7 was shown by increasing the sampling time from 167 to 500 sec—which is not a viable solution to fluorescence interference in the continuous wave system design. Time resolution of Raman and fluorescence peaks has been visualized by measuring the time between both the laser excitation pulse and Raman pulses and the laser and the fluorescence pulses, proving that Raman peaks do statistically show up earlier in time than those of fluorescence.

A sampling time for measurement of field relevant concentrations using a time resolved system according to one embodiment of the present invention is currently on the order of 500-1000 seconds per wavelength data point. This sampling time is applicable in long-term monitoring stations. In one embodiment, a sampling time of about 150 seconds to about 400 seconds is contemplated with one embodiment using about 240 seconds.

A system 50 for measurement of the constituents of a sample is shown in FIG. 1. Although a particular system 50 will be shown and described, the present invention further contemplates other embodiments, such as by way of example only, those using LEDs and incoherent light sources, charge coupled devices, avalanche photodiodes, Bragg gratings, holographic gratings, and related devices.

The low cost and unique capabilities of the system 50 include a diode laser, photon detection, and data acquisition technology. The system 50 consists of eight primary components. Excitation is provided using a Teem Photonics 532 nm Q-switched microchip laser 100 (~3 µj/pulse; ~400 ps pulse duration; ~6.4 kHz repetition rate). The excitation source is directed through a beam splitter 200 (custom built to specifications by OZOptics) to create a data acquisition trigger via a photodiode 300 (Hamamatsu S5973-02). Light that passes through the beam splitter is directed through a co-linear probe 400 containing focusing optics as well as a source wavelength filter on the return light path (InPhotonics RPB-532). The excitation source is then directed toward a sample contained within a custom chamber 500 which enables precise optical focus on a variety of test specimens. Scattered light is collected in a co-linear back-scatter geometry and guided into a CVI CM110 monochromator 600 and observed using a photomultiplier tube (PMT) 700 (Hamamatsu H7422) operated in a photon counting mode. PMT output is observed via an impedance matched BNC link to a 100-ps Time Digitizer 800 (Ortec Model 9353). In yet other embodiments of the present invention, the components best described are controlled by a controller (not shown), such as a digital controller. Further, in yet other embodiments, the output of PMT 700 is provided to the controller for signal processing and memory storage.

In the description of system components that follow, various specific examples will be provided. However, it is understood that these components, their characteristics, and their source of manufacturing and design are by way of example only, and other embodiments of the present invention contemplate system components with different characteristics provided by and designed by different manufacturers.

A green, passively Q-switched MicroChip laser 100 and 1100 was obtained from Teem Photonics (Part No. SNG-03E-000) for this system. The device is centered at 532 nm and emits 4 uJ/pulse, has pulse width 0.5 ns (FWHM), repetition rate of 5.9 kHz and bandwidth of about 0.5 nm. The laser head is portable, measuring a few inches on each side and weighing about 300 g. The laser in controlled by a microcontroller and cooled using a thermoelectric cooler, all packaged inside a hermetically sealed package. The laser also includes a controller unit (Part No. MLC-03A-DR0) that features a digital interlock and key-secured power control and indication LEDs. The laser head is mounted on a platform that accommodates assembly and alignment of the laser with the free-space to SMA coupler and beam splitter. In those embodiments including an electronic controller, the controller interfaces with and is operably connected to the laser controller for laser 100. Although a repetition rate of about 6 kHz has been shown and described, the present invention contemplates other repetition rates. Preferably, the duty cycle of the repetition rate (the fraction of time the laser is on compared to the period of time the laser is off) is very short, and provides sufficient time the fluorescence effects to die out before the next pulse is emitted.

Figure 2:
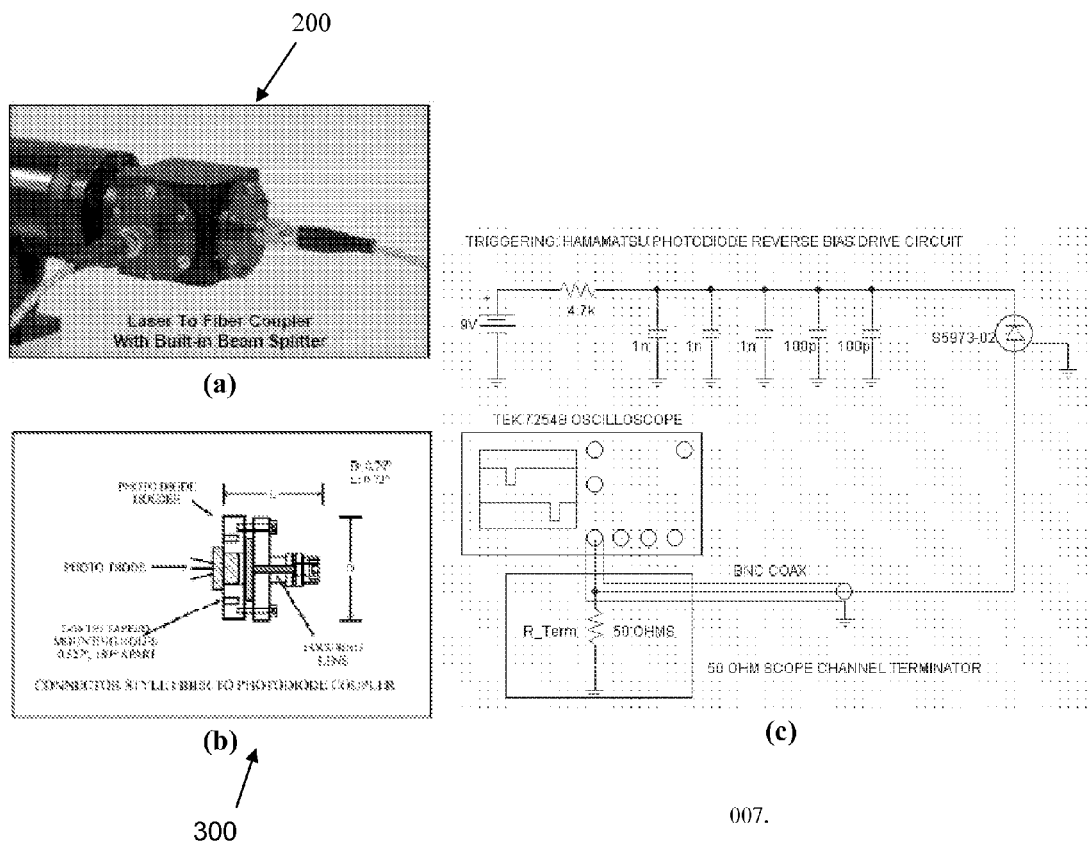
FIG. 2: A beam splitter/coupler according to the system of FIG. 1.

A beam coupler and splitter 200 and 1200 sits on a single housing that captures the laser light from free space and splits it and couples it into two separate fibers according to 79/21% split ratio (FIG. 2). The greater fraction of the light is passed via fiber to the Raman probe for sample excitation while the lesser fraction is passed via fiber to a photodiode which converts the optical signal to an electrical current. This PD signal is fed in parallel to the PMT output signal to the data acquisition unit (Tek TDS 7254B Oscilloscope—described later) and is used as a trigger for synchronous data acquisition. Such a trigger is used because the Raman signature exists while the laser light is on, which is for about 0.5 ns every 167 us (laser repetition frequency is ~6 kHz). Although a split ratio of about 4:1 has been shown and described, the invention is not so limited. The portion of light provided to the photodiode should be sufficient to trigger a detectable output from the photodiode. Further, the portion of light provided to the sample should be sufficient to result in a sufficient quantity of scattered photons for subsequent counting. Although a data acquisition unit comprising an oscilloscope has been shown and described, the present invention contemplates other methods of acquiring data including a computer 1800 with memory, as described elsewhere herein.

A photodiode 300 and 1300 is used to facilitate optical-to-electrical conversion in order to use the laser pulse as a trigger for the data acquisition system. The photo diode used is a Hamamatsu S5973-02 and has the following properties: range: 320-1000 nm, reverse bias $V_{MAX}$=20V and 0-1 GHz frequency response. The photodiode is coupled to the fiber from the beam splitter using a fiber to photodiode coupler from OZOptics (FIG. 2($b$)) and wired in a reverse-bias fashion using a circuit shown in FIG. 2($c$). Actual measurements show that the rise time of the PD is about 0.5 ns and the slew rate is ~4.2 GV/sec, which is comparable to both laser rise time and the PMT response time, making it suitable for a triggering operation.

Figure 3:
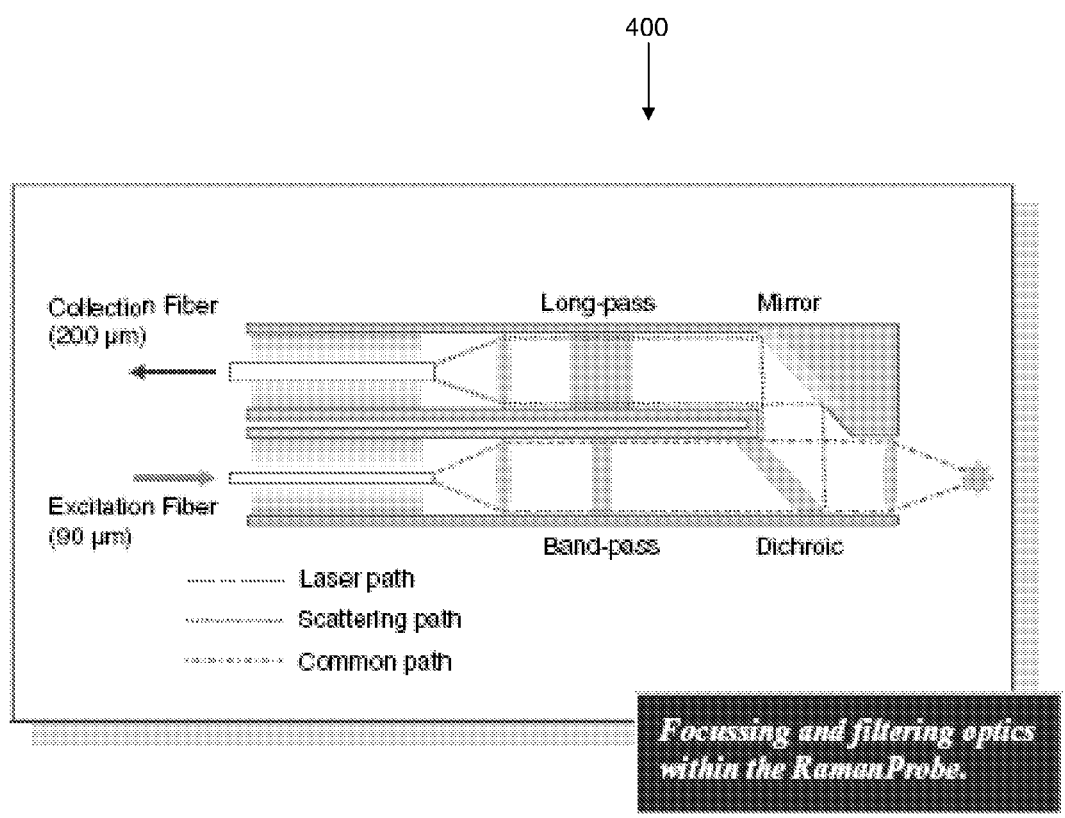
FIG. 3: A Raman optical layout according to the system of FIG. 1.

Some measurement systems use a "Raman microscope" to collinearly excite and collect the scattered light. System 50 and 1500 utilizes a smaller, compact and durable probe 400 and 1400, respectively, from InPhotonics, Inc. This probe, shown in FIG. 3, includes filtering of the incoming laser to a predefined excitation band, a pass through a dichroic mirror which allows the laser to pass through one way and focus onto the sample via a lens, but reflects the back-scattered photons.

The return signal is then filtered through a long-pass filter which removes all frequencies at and above that of the laser, effectively removing Rayleigh and anti-Stokes scattering, leaving longer wavelength Raman and potentially fluorescence signatures.

The probes excitation fiber is 105 um and the collection fiber is 200 um in diameter—both are outfitted with SMA connectors, which match the monochromator and laser fiber sizes and formats. Further, this Raman probe is made of durable stainless steel with a sealed focusing lens at the tip which focuses the light to a fixed focal distance of 7.5 mm. In order to have adjustable focus onto the surface of the solids or deep enough into liquids, a hollow screw adapter enables the probe to be positioned in a horizontal line in and out of the sample chamber although other embodiments contemplate the probe being positioned in other orientations, including vertically. Probe 400 also incorporates a manual safety shutter.

Figure 4:
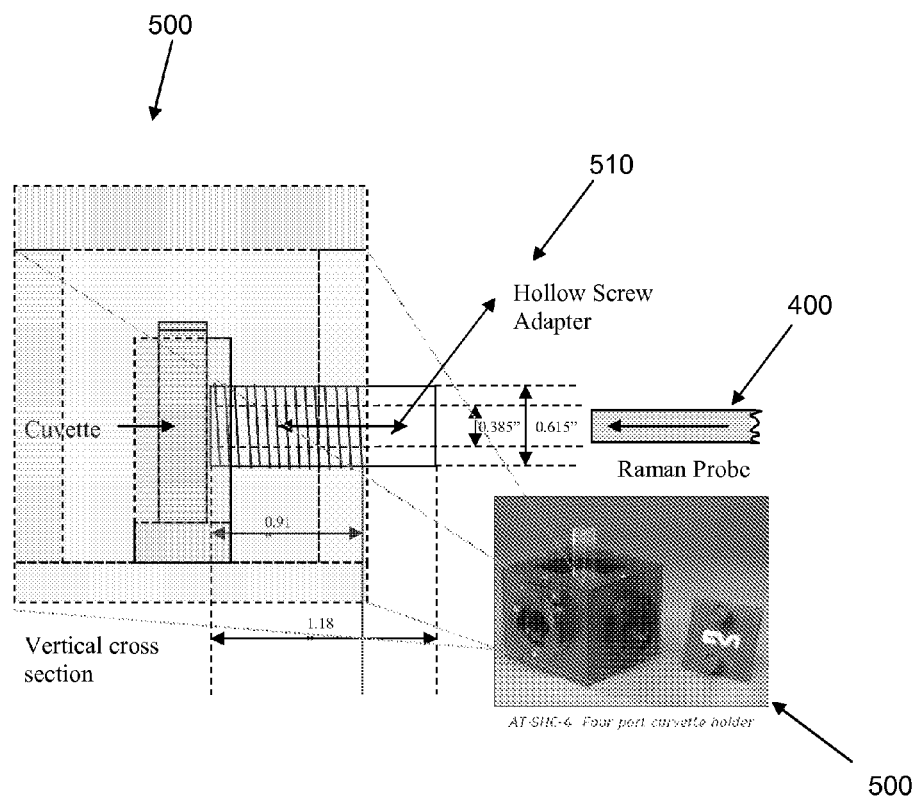
FIG. 4: A sample chamber detail according to the system of FIG. 1.

A light tight sample chamber 500 and 15—was obtained from Spectral Products, Inc. (AT-SHC-4) and accommodates both collinear and 90 degree excitation and collection angles. It features a black-anodized aluminum container (FIG. 4) outfitted with 4 ports normal to each other and all in the same horizontal plane for both collinear (transmission and reflection) and ninety degree (scattering) measurements. All four ports are configurable for open space optical transmission or SMA connectors (fiber to free space light de-coupler) with a focusing optic at the connector as well as in front of the sample cell.

A sample is interrogated in a standard fluorometer cuvette 12.5×12.5×45 mm which fits in the central compartment of the sample chamber. Starna Cells, Inc. was chosen as a supplier of a 3-Q-10 Far-UV Spectrosil® Quartz cuvette with a range of 170-2700 nm and a path length of 10 mm (App. B).

The sample chamber was retrofitted with a hollow screw adapter 510 (shown in FIG. 4) instead of an SMA fiber de-coupler in order to allow the Raman probe to be inserted into the chamber. This also gives the probe extra fine depth-of-field adjustment to enable investigation of different sample types.

Finally, a custom top was designed and manufactured for the sample chamber in order to fit screw-top type cuvettes which are taller. This top prevents the stray light from entering the chamber and interfering with the measurement as well as spreading of the potentially dangerous reflections of the laser light. Other ports are closed off when not in use.

The scattered light that is collected by the Raman probe 400 and 1400 is transmitted via the collection fiber and positioned onto the entrance slit of the monochromator 600 and 1600, respectively, using a small XYZ stage that can both center the beam of light (X, Y degrees of freedom) as well as focus it at a particular distance in space (Z degree of freedom). Although the laser is a monochromatic source, depending on the chemical composition of the sample under test, many different (lower energy) longer wavelengths may appear due to the fact that different molecular bonds can have different resonant energies and will thus emit light with less energy compared to that of the excitation source. This means that what comes out of the probe can have many different frequency components and therefore, intensity is wavelength dependant. The light is separated into frequency components before the detector 700 and 1700 measures the intensity.

A monochromator is a device that spatially separates polychromatic light such that its frequency components are no longer convolved in space (contained within the same volume of space), but are rather angularly separated over a larger distance.

Monochromator 400 and 1400 is a CM110 single pass, ⅛ meter, computer-controlled monochromator/spectrograph from Spectral Products, LLC. In those embodiments including a controller, the controller interfaces with and is operably connected to the controller of monochromator 400. The CM110 is a Czerny-Turner type monochromator with dual-grating turrets, focal length of 110 mm, f/#=3.9, options for a straight through or 90 degree light entrance and exit path (the prototype makes use of a straight through path geometry), interchangeable slits (25 um slits are typically used), and the resolution was <1 nm with the 1200 grooves/mm (part no.: AG1200-00850-303) gold coated grating (Spectral Products Inc., 2003). Although what has been shown and described is a monochromator of the Czerny-Turner type, the invention is not so limited and contemplates the use of any monochromator. Preferably, the present invention includes monochromators that are capable of being controlled by controller 1800 with regards to their band-pass characteristic.

Figure 5:
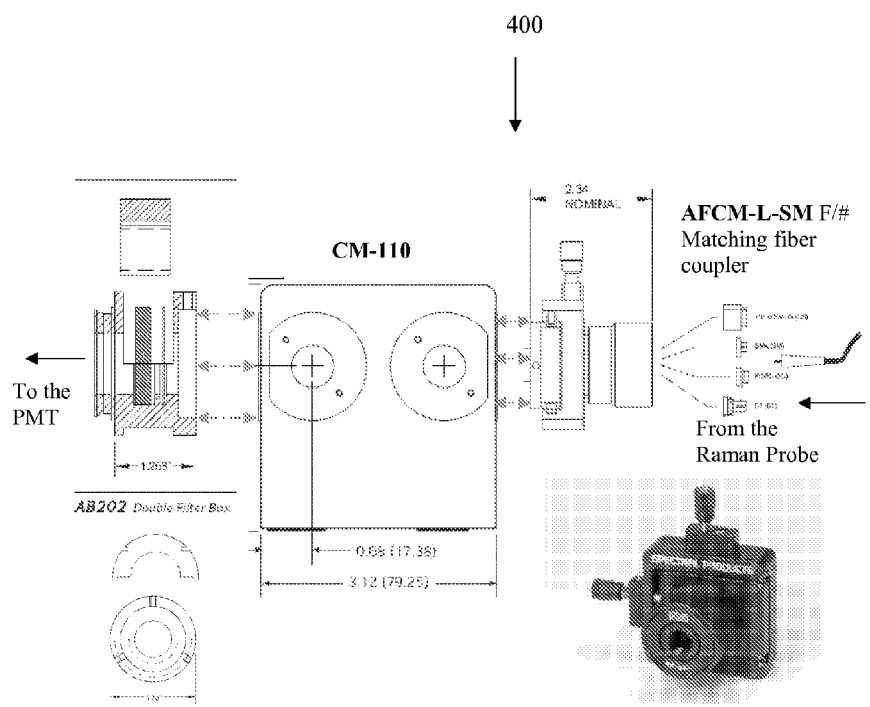
FIG. 5: A CM-110 monochromator setup according to the system of FIG. 1.

Monochromator 400, along with its adjoining components is shown in FIG. 5 below. Not shown, but included in the setup are the power supply (60 W, 5V/7 A, 15V/3 A) and the serial interface and cable to the computer controls.

An f/# matching fiber coupler is used to match the numerical aperture of the collection fiber (NA=0.22) to the f/# of the monochromator. Because this coupler focuses the light onto the slit using X, Y & Z adjustments, the efficiency of coupling to the grating is 2 to 40 times better than in a non-matched case. The three micrometer-style translation stages achieve up to 0.001" precision, and the coupler is efficient in the 200-1900 nm range.

An AB-202 filter holder with a collimating lens takes the light from the output slit of the CM-110 monochromator and channels it to the PMT through a series of optional filters that can be inserted into the holder. This holder fits filters 1" in diameter, one 2.5 mm and one 0.25" in thickness. The main purpose of this holder in this setup is to channel light to the PMT and to hold neutral density filters used during instrument calibration procedures. Although specific apparatus has been shown and described, the present invention is not so limited and contemplates other types of components for providing the collected, filtered, inelastically-scattered photons to the counting sensor.

System 50 and 150 further includes a sensor for detecting and counting individual photons. In one embodiment, system 50 includes a photo-multiplier tube 700 and 1700, respectively, such as photo sensor module H7422P-50 or -40, by Hamamatsu Photonics. The device incorporates a photo multiplier tube and a thermoelectric cooling unit (Peltier element). This device is used to detect and count photons coming from the Raman probe via the monochromator.

In one embodiment, a photo-multiplier tube (PMT) 700 and 1700 is an amplifier that operates in the region around visible light frequencies. For model H7422P-50, this range is from 380 to 890 nanometers (789.47-337.08 THz). Within the device, a light sensitive material is used for a photo-electric conversion based on the principle of photoelectric effect. This material can be an alkali metal, but in the case of a high sensitivity photon-counting tube such as the one used in system 50, it is a Gallium-Arsenide (GaAs) semiconductor. This material offers higher cathode radiant sensitivity than alkali metals (at 550 nm it is 68.7 mA/W), which allows for higher sensitivity and enables counting of single photon events. This PMT also features very low dark current (70 pA), 1 ns rise time, and portability due to thermoelectric cooling in the range of 0-35° C.

Figure 6:
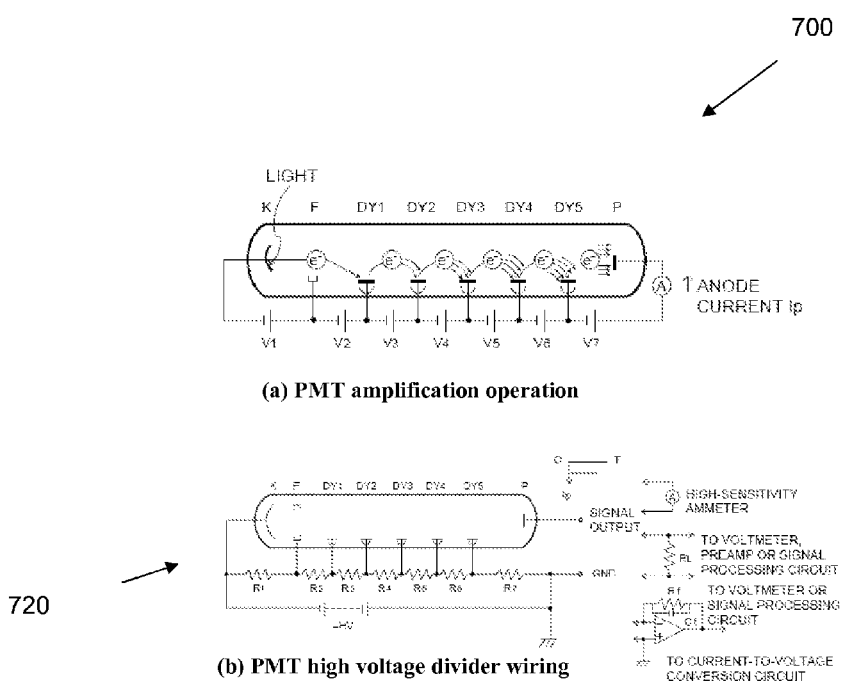
FIG. 6: A principle of operation of a photo multiplier tube (PMT) according to the system of FIG. 1.

FIG. 6a shows a schematic detailing the primary components of a PMT. The photo-sensitive cathode (K), which is made from GaAs performs the photo-electric conversion by ejecting one electron for every photon that is incident onto its surface. This electron is received by the focusing electrode (F) and focused onto a series of dynodes which act as amplification stages. This amplification happens as a result of a high potential difference (500-3000 V) that is setup between the cathode and an anode (P)—the last electrode at the receiving end of the dynodes.

Further, a potential gradient is setup across dynodes so that when the first dynode is hit by one electron ($e^-$), its gain, $G_{D1}$ produces and ejects $G_{D1}*e^-$ electrons, which are then accelerated towards the second dynode, which in turn causes $G_{D2}*G_{D1}*e^-$ electrons, and so on until the anode is reached. This potential gradient can be setup, with multiple voltage sources between dynodes, although in some embodiments this is done with a voltage divider 720 (see FIG. 6(b)) made up of resistors that apply a particular distribution of voltages, depending on the particular PMT application (Hamamatsu, 1999).

Typical PMT gain is generally above $1 \times 10^6$, and is dependant upon the incident wavelength and quantum efficiency (QE) of the photocathode. QE is calculated from the cathode radiant sensitivity (S), which is measured in amperes of (electron) current per watt of incident photons. These are related according to the following formula:

$$QE = S \times 1240/\lambda \text{ (1240 is } \lambda \text{ in vacuum corresponding to 1 eV.)} \quad (1)$$

QE represents the probability of a photoelectron being emitted when one photon strikes the photocathode, which can range from 0 to 1. In other words, QE refers to the ratio of the average number of electrons emitted from the photocathode per unit time (measured in Amps) to the average number of photons incident on the photodiode (measured in Watts).

Gain correction can be considered if the PMT is used over a broad range of wavelengths since the cathode radiant sensitivity, S varies across the spectrum. Further, gain is also controlled by the control voltage input, which ranges form 0.5 to 0.8V. In some embodiments, this gain is controlled by the system controller.

Figure 7:
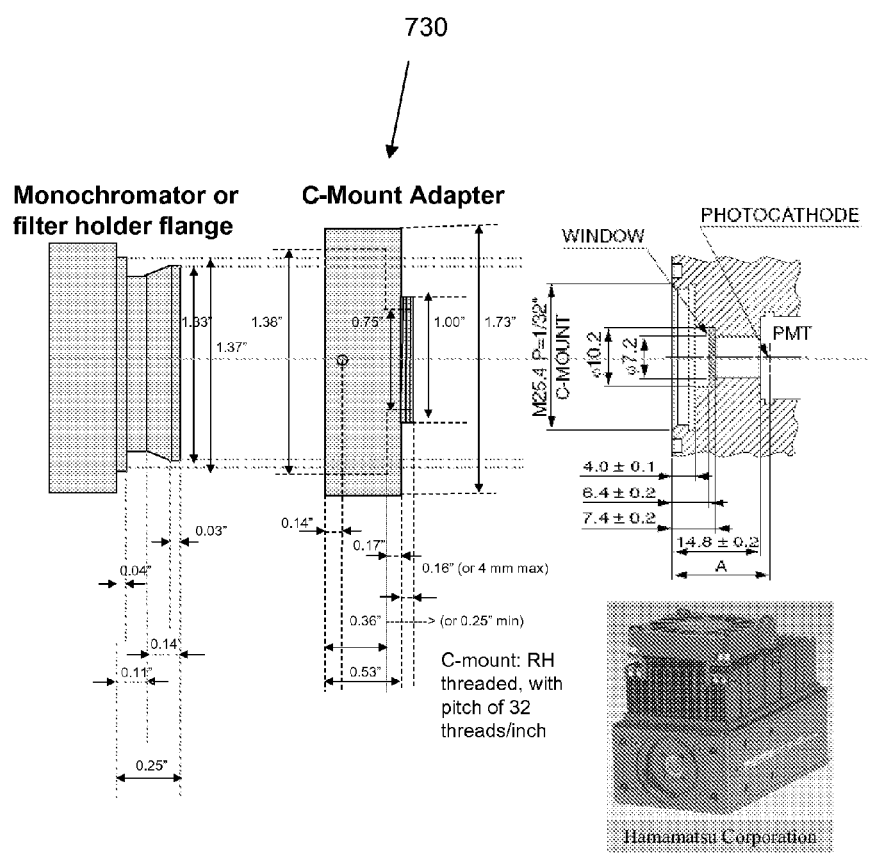
FIG. 7: A PMT-filter box (C-mount) adapter according to the system of FIG. 1.

The PMT is interfaced in free space to the filter box via a "C-Mount" adapter 700 that attaches via a threaded C-type mount to the PMT on one side, and via 3-screw clamp to a flange on either the filter holder or directly on the monochromator. This setup is shown in FIG. 7.

Not shown, but included with the PMT are its power source and control voltage PC board, control and signal cables along with a simple custom-built board for wire routing, burn sound warning and protection and indicator LEDs. PMT power (+12 V, ~400 mA) was supplied using an Agilent E3620A 0-25V, 0-11A Dual Output Power Supply, and the control voltage was monitored using an Agilent 34401A Digital Multimeter.

PMT 700 and 1700 acts as a current source due to the fact that photons produce electrons which are multiplied over dynodes and exit out of the anode, thus making a negative conventional current appear at the PMT output. This current is small, ranging from 70 pA to 2 uA maximum. Such currents at the output may need special detection capability due to amplitudes comparable to noise in the surrounding equipment, power lines and signal cables.

Due to the ability to resolve Raman from other unwanted photons, and because theory dictates that the Raman phenomenon occurs earlier in time relative to other optical interference, it is possible to achieve a statistical improvement in Raman signal relative to noise by performing photon counting. Raman photons theoretically show up before all others, even if there is some uncertainty and overlap with photons from other phenomena in experimental observations conducted with a finite observation window and excitation pulse duration. Given that Raman photons have a much smaller probability of occurrence than fluorescence, it is beneficial to increase the sampling time to accumulate a larger number of Raman-scattered photons. Provided that the statistically significant temporal separation is achieved, Raman photons, even if infrequent, should outnumber the noise photons if the system "waits" long enough for enough of them to be scattered, provided that there are sufficient molecules to yield Raman photons in greater quantity than the darc count of the measurement system.

The impact of a photon upon the sensing surface of the PMT creates a signal of a certain intensity at the output of the PMT, based on the gain of the PMT and the loading characteristics of the readout device (such as a controller 1800). In some embodiments, there is a computer-controlled threshold voltage, and if the magnitude of the PMT signal does not exceed the magnitude of this adjustable cutoff, then the PMT signal is ignored. This adjustable cutoff provides for the ability to reject electrical noise, including random emissions from the photo-multiplier tube.

Figure 9:
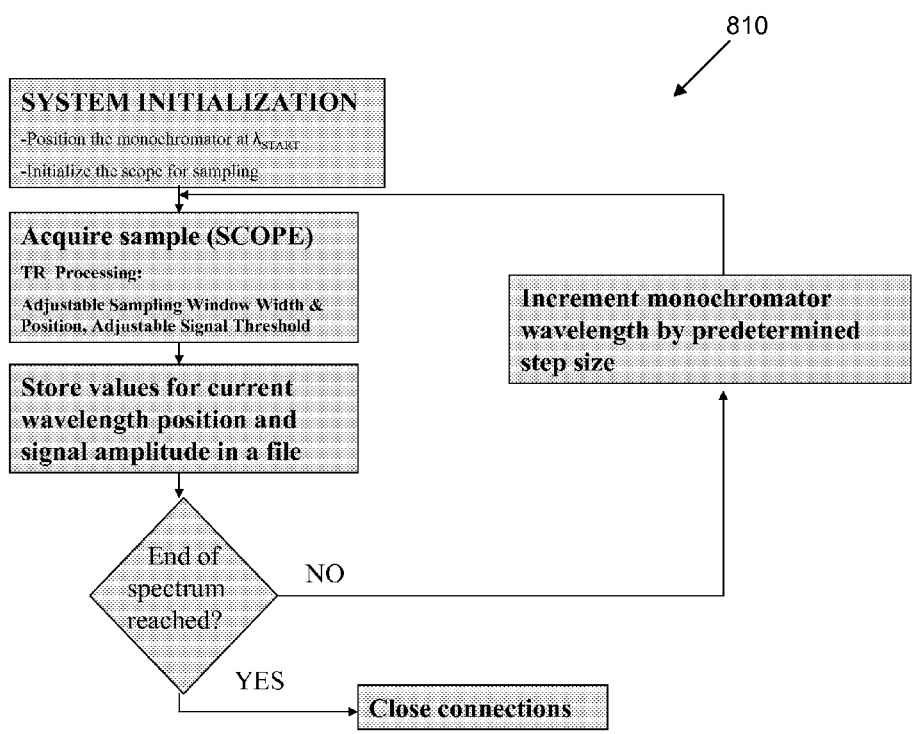
FIG. 9: Time-resolved spectrum acquisition algorithm according to the system of FIG. 1.

Increasing the sampling time in continuous wave regime does not markedly improve Raman peak SNR. With time resolution (TR), there is a marked difference in terms of improvement in SNR with the increase in sampling time. This is shown in FIG. 10(*b*), where nitrate solution at the concentration of 5000 ppm is sampled for different lengths of time using the TR system. It can be seen that the peak SNR increases linearly with increase in sampling time, proving that Raman photons, however infrequent, do arrive earlier on average compared to the "noise" photons ("noise" in this context referring to fluorescence or phosphorescence, and not random electrical signals). This graph also shows minimum sampling time of 8.3 sec per point to extract the Raman peak from the 5000 ppm concentration with an SNR>=1. FIG. 9 presents a block diagram representation of acquisition logic 810 according to one embodiment of the present invention.

Figure 8:
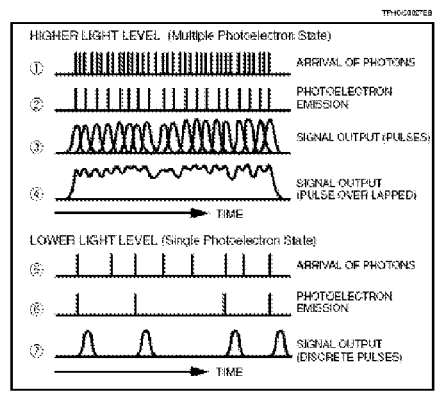
FIG. 8: A PMT signal output properties & detection according to the system of FIG. 1.
Figure 8:
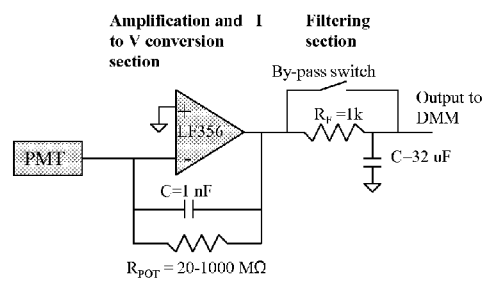

The H7422P-50 PMT has two modes of operation—analog mode and digital (photon counting) mode. FIG. 8(*a*) best depicts these two modes based on the frequency of incoming photons into the PMT. At lower light levels, where single photons enter relatively infrequently (when pulse-to-pulse interval is much longer compared to the pulse width (about 2 ns at FWHM—rise time is 1 ns), photon counting mode is possible and preferred due to its better SNR and stability compared to the analog mode. It is also called digital mode since the post-processing circuitry will make binary decisions (counts) based on the presence of individual peaks.

However, once photons start arriving at a more frequent rate and the pulse-to-pulse interval becomes comparable to, or shorter than the pulse width, pulses start to overlap and create an average current with shot noise fluctuations. When a continuous wave (CW) laser is used, there is a powerful and continuous excitation of the sample and both Raman and fluorescence photons are constantly arriving at the PMT, forcing the sampling into analog mode.

In system 50 and 150, the PMT is utilized in photon counting mode. Utilizing the pulsed laser and seeking time-resolved Raman measurements where single photon events can be counted, an ATD converter captures and stores PMT data in sync with the trigger since the target phenomena occur on the sub-nanosecond scale. In order to perform initial measurements with the system, a Tektronix TDS7254B Programmable Oscilloscope was chosen as the data acquisition unit. However, as described elsewhere, it is also possible to use computer controllers such as computer 1800 incorporating a digitizing card. This digital oscilloscope features 2.5 GHz, 20 GSamples/sec GPIB acquisition boards, a programmable interface to Windows XP PC contained within the unit and an easy to use front panel and color LCD touch-screen. This device could be substituted by any of an array of off-the-shelf high bandwidth data acquisition cards or multi-channel scalers.

The laser trigger obtained through photodiode 300 and 1300 is used as a reference to indicate when Raman and fluorescence peaks are likely to occur. This signal, which ranges from 0 to −3V (diode is reversed biased) is fed into the channel 1 input of the scope via a 50 ohm port terminator so that the PD and the scope are matched (or the diode signal in other embodiments of the present invention is provided to a computer controller 1800). The photodiode is matched to 50 ohms, and coax BNC cable was used along with EMI shielding and careful layout of all PD circuit components to minimize parasitic capacitance and maintain within acceptable limits the rise time of the laser that is presented to the scope. The PD signal generally defines when the oscilloscope should start its scan, and overall system jitter is partly defined by this component.

Photon counting is performed on channel 2 of the scope using a 50 ohm port terminator as a load resistor for the incoming PMT signal which is acting as a current sink. Since the pulsed laser does not continuously excite the sample, photon emission events (whether Raman or fluorescence) are rare enough such that the photon peaks do not overlap and create a continuous current but rather show up as individual peaks so that single events can be seen on the oscilloscope, or provided to the input circuitry of a computer 1800. Photon events appear on the PMT as peaks about 2.5 ns wide, and for most chemicals are about 10-20 mV. While Raman peaks are generally single photon events due to the low probability of occurrence, peaks can be much larger in the presence of fluorescence where multiple photons hit the photocathode at the same time and cause a larger peak at the output.

The existing prototype makes use of short (less than about 500 picoseconds), high repetition rate (~6.4 kHz) laser pulses and rapid detection gating to effectively resolve Raman signatures prior to fluorescence in the time domain, with enough statistical significance to improve detection levels of target compounds that otherwise would be obscured by the presence of fluorophores.

To calibrate the system and demonstrate that it can indeed obtain accurate Raman spectra, tests of standard compounds such as benzene were performed. As illustrated in FIG. 10*a*, the system produces an accurate representation of the relative peak heights and locations for the calibrations standard, which in this case was chosen as benzene. The top plot of FIG. 10*a* presents the Raman signature as determined by system 50. The bottom plot presents a published standard.

Figure 11:
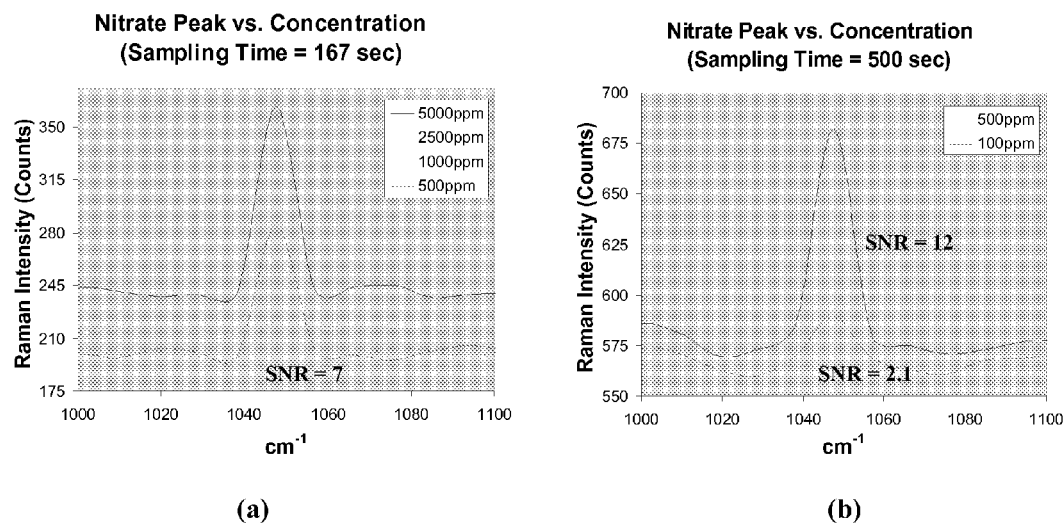
FIG. 11: Nitrate peak amplitude as a function of concentration in TR mode.

Since system 50 makes use of a photon counting signal acquisition algorithm the system can effectively separate Raman photons from background noise. In FIG. 11, where a nitrate solution at the concentration of 5000 ppm is sampled for different length of time using the time-resolved system it can be seen that the peak signal-to-noise ratio of the system increases linearly with an increase in sampling time.

Figure 12:
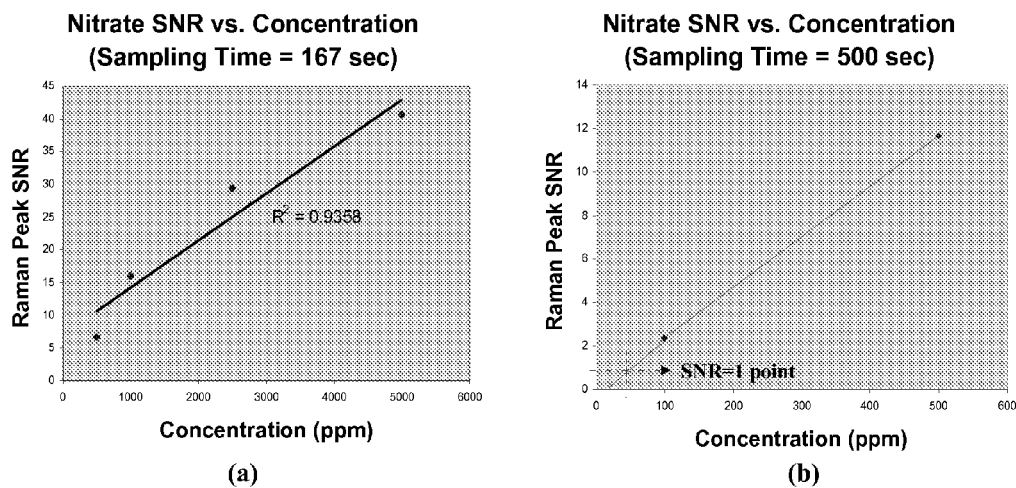
FIG. 12: Nitrate peak SNR as a function of concentration in TR mode.

FIG. 11 shows the effect of concentration on peak amplitude, demonstrating that lower concentrations can be detected. Lowest detectable concentration using the initial sampling time of 167 sec was 500 ppm. Exploiting the statistical model for improvement of Raman SNR, sampling time was increased from 167 sec to 500 sec per wavelength step, and Raman signature indeed improved in SNR. As it can be seen in FIG. 11(*a*), smallest Raman peak was observed at concentration of 500 ppm with the SNR of 7. Testing this same concentration with 500 sec shows a marked improvement in SNR to 12, as shown in FIG. 11(*b*). Further, this sampling time allows detection of even lower concentrations, such that 100 ppm is now observable with the SNR=2.1. Because this SNR is still distinguishable from the noise floor, a projection of smallest detectable concentration at this sampling time interval can be made. This is shown in FIG. 12 where SNR=1 point occurs at 50 ppm. Increasing sampling time can further improve this "limit". Further improvements can be had by improving the sensitivity of the photon-counting detector, increasing the power of the pulse of light, reducing electrical noise in the system, and similar techniques.

Further, as FIGS. 10*b*, and 11 show, increasing the sampling time increases the sensitivity of the system in a linear fashion, implying that an order of magnitude increase in sampling time results in an order of magnitude improvement in detection rate. This is directly observable from FIG. 10*b*. It is possible that the detection limit for sampling time of 5000 sec would be roughly 5 ppm, which may be in the relevant range of macronutrients.

Figure 13:
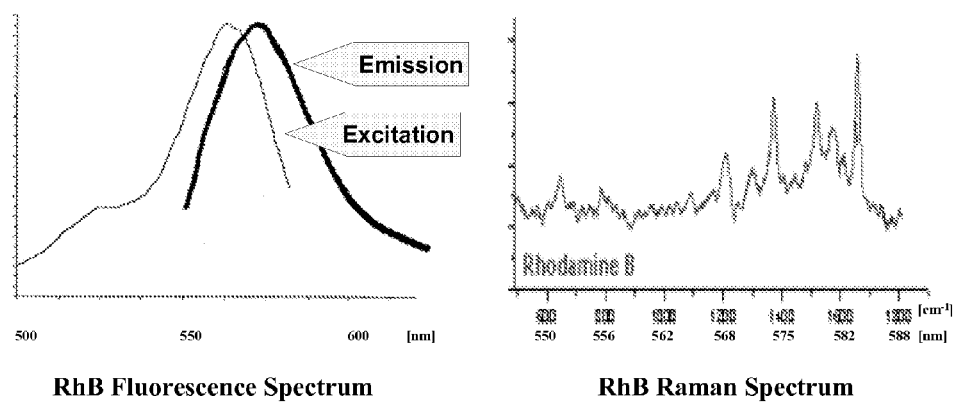
FIG. 13: Rhodamine B spectrum properties.

While detection of low concentrations of relatively simple solutions is shown above, system 50 also has the ability to distinguish a Raman peak even amidst considerable fluorescence. To simulate one scenario, a common calibration chemical, benzene is doped with Rhodamine B, which, as FIG. 13 shows absorbs and emits in the 532 nm range. Because RhB is used a fluorescing tracer for biological purposes, its effect on Raman sampling even in TR mode can be overwhelming, and unmanageable in a continuous wave system.

Figure 14:
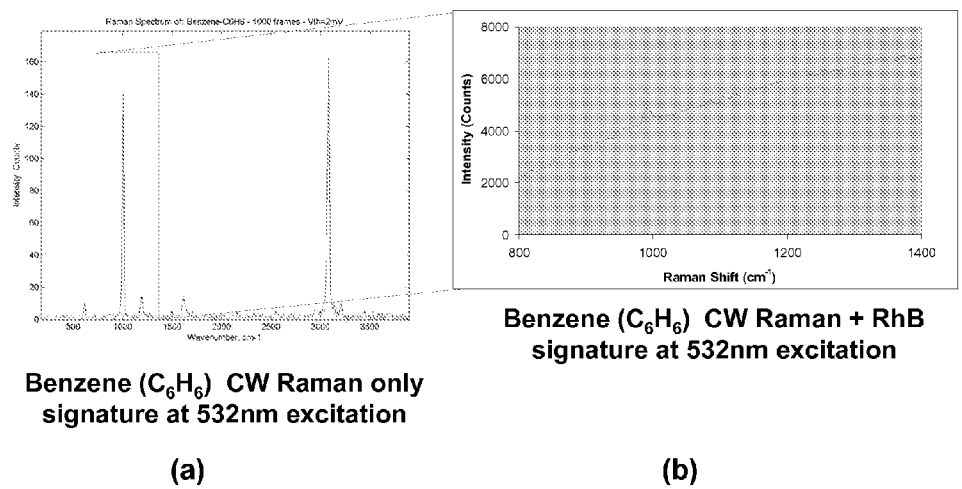
FIG. 14: Fluorescence interference caused by RhB in benzene.

Degradation of Raman peak SNR is clear from FIG. 14, where a spectrum of benzene is shown before and after addition of RhB dye. It should be understood that this sample considers nearly an extreme scenario of fluorescence, as RhB does not exist in nature, and its fluorescing properties are much stronger than any organic medium commonly known to fluoresce in soil samples. By experimenting with this scenario, TR system capabilities are put to the test and illustrate that more manageable samples can be successfully handled with less effort, shorter sampling time and lower concentrations can be achieved.

Figure 15:
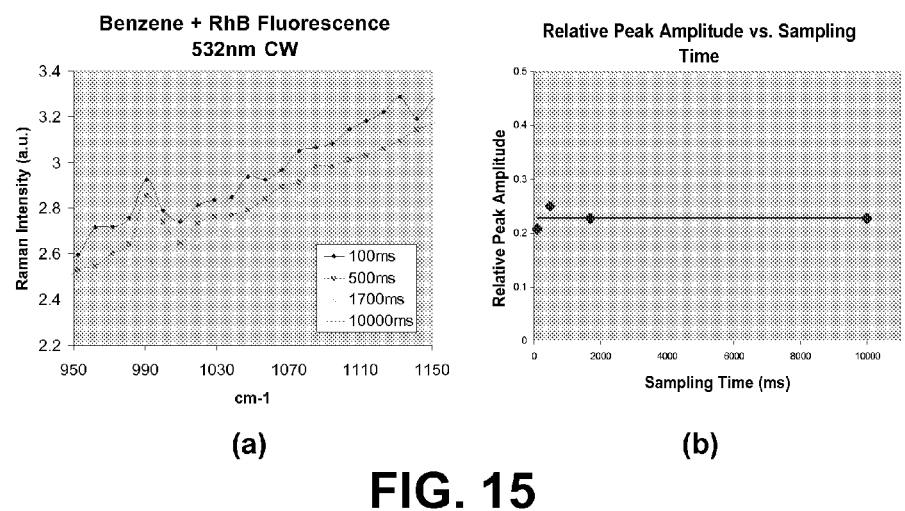
FIG. 15: Lack of improvement of SNR with increasing sampling time in CW case.

To illuminate the advantage of using a TR system for rejecting fluorescence, comparisons is done between CW and TR system by testing the Rhodamine doped benzene discussed above. FIG. 15 shows a series of tests of RhB benzene on CW system, where an attempt is made to increase the signal-to-noise ratio of the (barely visible) benzene Raman peak, which would translate to ability to detect lower concentrations. FIG. 15 (a) shows Raman scans using different sample times and shows that increasing the sampling time does not increase the SNR. This is shown in FIG. 15 (b), where peak amplitude is not influenced by increase in sampling time, as suggested by the zero-slope line-fit.

Figure 16:
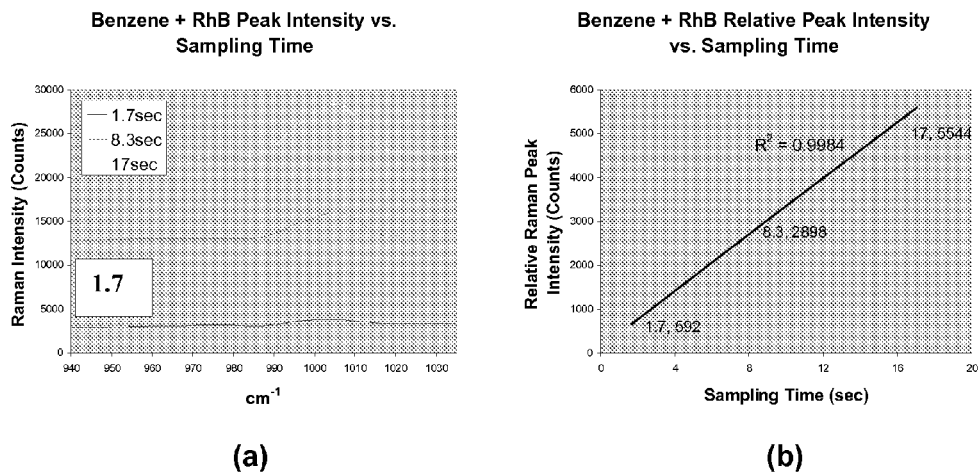
FIG. 16: Improvement of SNR in the presence of fluorescence according to one embodiment of the present invention in TR mode.

Performing a similar test using the TR system, Raman peak intensity scales with sampling time, implying that despite overwhelmingly large number of fluorescing photons, Raman photons still statistically arrive earlier, and can be distinguished from fluorescence, given enough accumulation time. This is shown in FIG. 16 where Raman peaks increase in amplitude with increase in sampling time. Moreover, FIG. 16(b) shows that the relationship is linear, so that when sampling time is doubled, the peak amplitude (and SNR) also doubles.

Figure 17:
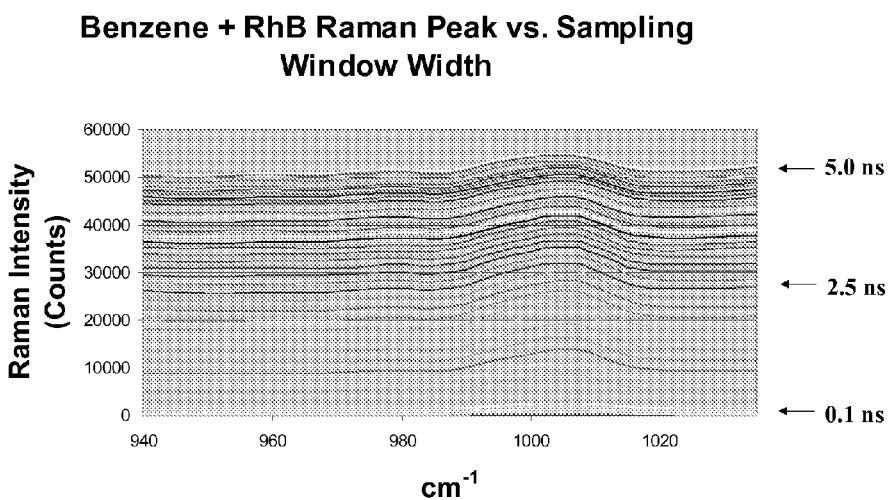
FIG. 17: Parametric study of benzene doped with rhodamine B fluorescing medium as a function of window width.

FIG. 17 illustrates the affect of moving a data acquisition sampling window with respect to the laser trigger. In this figure sampling window width following a consistent delay from the trigger signal of the system is varied from 0.1 to 5.0 ns.

As the window width is varied there is a notable change in the Raman SNR of the benzene peak. It is noticeable that not all spectra have the same Raman peak amplitude, and that varying the window width increases the peak SNR from zero to some maximum value (at a window width of approximately 2.3 ns) and then back down. This observation demonstrates that there is an optimal window width that isolates the most Raman peaks from those resulting from fluorescence and this is where the optimal temporal separation occurs. Observation windows ending earlier than this time will reject some Raman photons and a window larger than this value will start allowing some fluorescence peaks into the observation and degrade the Raman SNR.

Figure 18:
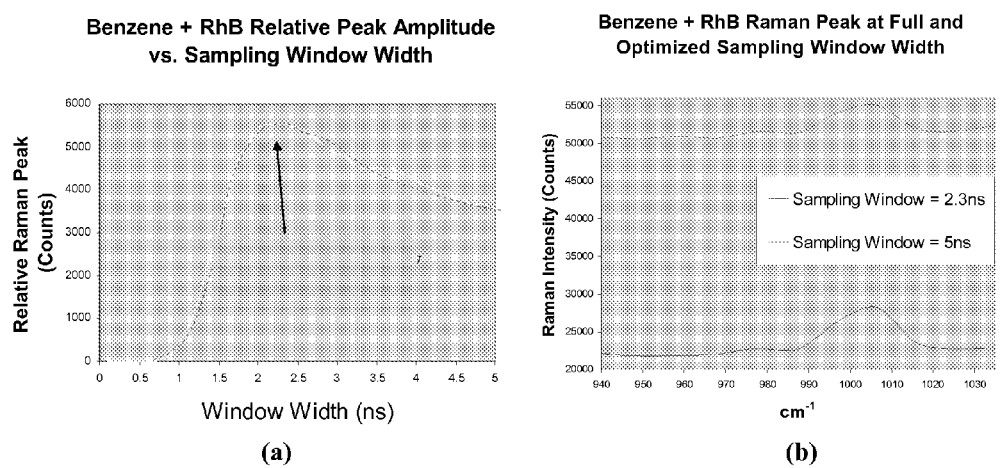
FIG. 18: Improvement in benzene peak SNR as a function of window width.
Figure 19A:
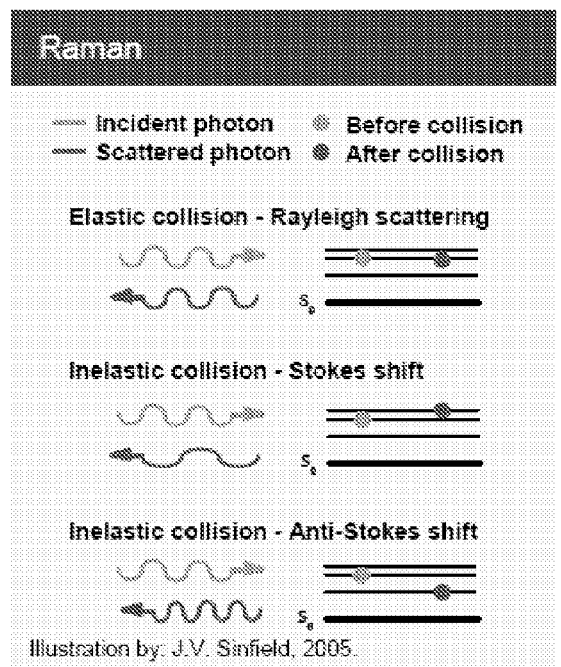
FIG. 19: Theory of Raman scattering and fluorescence emission.
Figure 19B:
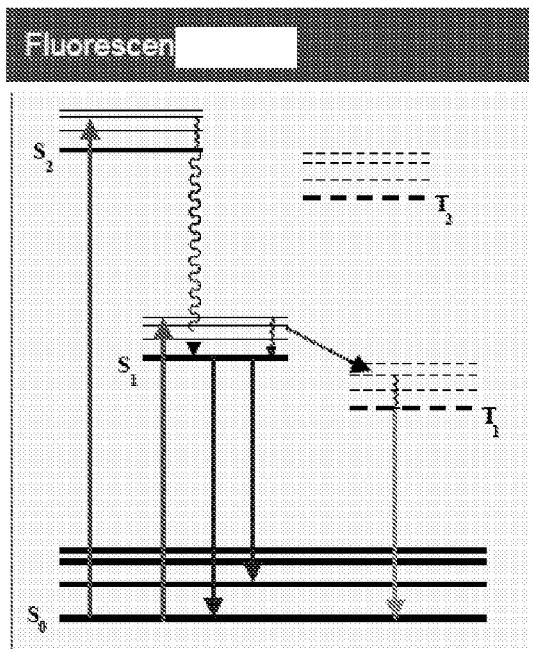

Optimal rejection was accomplished with a window 2.3 ns wide and this can be observed in FIG. 18, where relative Raman peak amplitude is plotted versus window width, and it can be clearly concluded that there exists an optimal point for Raman window placement. FIG. 18(b) shows a spectrum acquired using the full 5 ns wide window and also using an optimized 2.3 ns window. There is a clear improvement in difference in SNR between the two scans, illustrating the benefits of time separation of Raman and fluorescence photons in the time-resolved system.

The improvement in signal to noise ratio obtained by increasing the sampling time is limited. It is believed that there is a sampling time that includes the maximum ratio of Raman photons to fluorescence photons. Any other window will have increased noise or decreased signal. However, the optimum window may also be a function of the duration of the laser pulse and the dark noise of the detector. As discussed above, an optimum window was found to be about four to six times the duration of the laser pulse. Changes to these process variables likely result in changes to the width of the window, and possibly also to other window and timing parameters.

Figure 23:
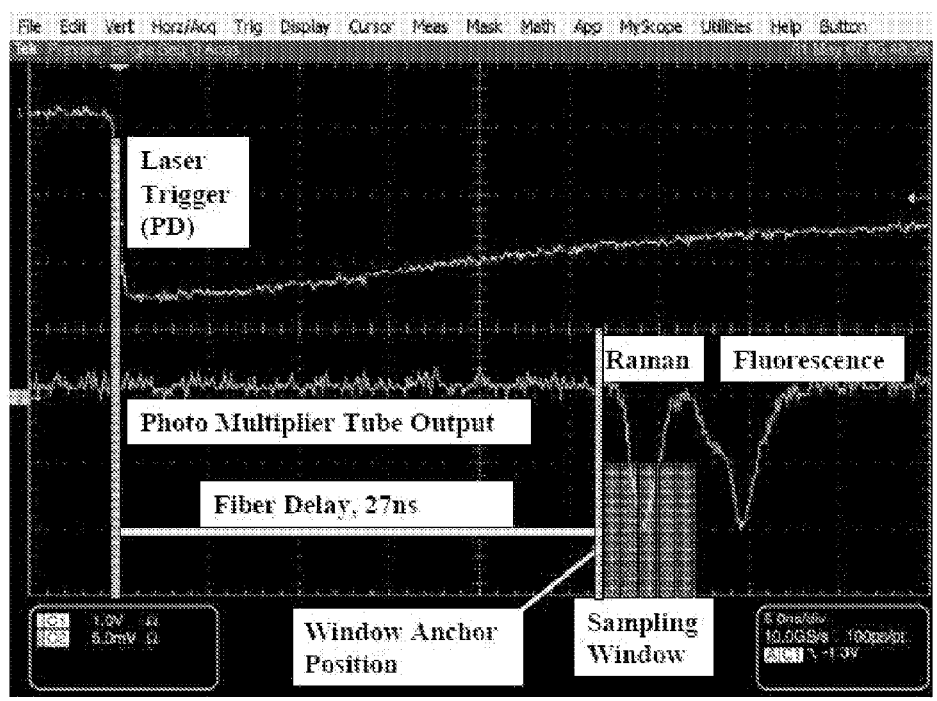
FIG. 23: Example of the sampling window in TR system according to another embodiment of the present invention.

Placement of the sampling window with respect to the laser trigger as well as its width can affect the performance of the system and SNR. To illustrate the motivation for window size and position optimization, FIG. 23 shows a screen shot of the oscilloscope trace capture of the laser trigger and the PMT output. After the laser trigger (PD on Channel 1) crosses the negative trigger threshold, the scope captures data points on Channel 2 and retains only those specified by the sampling window. Thus, when a pulse crosses the voltage threshold (the threshold to the scope, or in other embodiments, the threshold to the digitizing card or other memory hardware) the pulse is counted digitally only as a "peak." This way, each photon gives one count. This window, in one embodiment of the present invention, is anchored at the time position of 27 ns after the laser trigger because observations show that there are no earlier Raman peaks, except for spontaneous emissions. Note that the position of the window can be specific to the length of cabling involved, or other factors that can cause a delay in the arrival of the signal. Window width however, is adjustable from 0.1 to 5 ns wide, and the Raman spectra are reported as series of spectra with different window widths so that the operator (or data processing algorithm) can search for optimal window width that leads to the best SNR and therefore best separation of Raman and fluorescence phenomena.

The lower right portion of FIG. 23 shows the dual negative going peaks for both Raman and fluorescence (as labeled). Note that the Raman peak is well within the sampling window, this window beginning about 27 ns after a triggering signal from the laser diode. Note that the second, negative going fluorescence peak falls outside the window. For the particular picture shown in FIG. 23, there is a single peak for the fluorescence signal. However, as discussed elsewhere, this peak can be significantly larger and wider, depending upon the fluorescence and phosphorescence characteristics of the sample. Not shown on FIG. 23 is the adjustable voltage threshold, which would appear as a horizontal line with a magnitude greater than the substantially constant electrical noise appearing at the PMT output during the 27 ns delay.

Window width was initially arbitrarily set at 5 ns in order to include all peaks that are possibly Raman in origin. Although in reality, Raman photons only last about 500 ps (for the duration of the excitation pulse), the PMT broadens the response peaks due to its limited bandwidth and rise time, so that most of the PMT peaks end up being approximately 2.5 ns at FWHM).

In yet another embodiment of the present invention, there is a computer 1800 for acquiring data from system 150, such as a computer comprising an Ortec Model 9353 100-ps Time Digitizer/Multi-Channel Scaler plug-in Peripheral Component Interconnect (PCI) card. This device cost approximately ⅕ of the cost of the oscilloscope previously used for data acquisition and enables much more rapid analysis with data capture burst rates up to 1 GHz and sustained rates up to 10 MHz, allowing the system to monitor each of the laser's more than 6000 pulses per second. The card observes the amplified output signal of the Raman system photo-multiplier tube (PMT 700). Data acquisition is triggered by an input pulse derived from a photodiode 300 that intercepts approximately 21% of the light emanated from the system source laser as it passes through a beam splitter 200. This trigger initializes a chain of 1000 time bins subsequent to the trigger pulse which are each 100 ps in duration. The card then counts the number of PMT pulses (which result from photon detection) that exceed a voltage threshold that is set to reduce the detection of noise and maximize the detection of desired Raman photons. Based on observation of the PMT output, this voltage threshold has been set at −10 mV to conservatively eliminate counts that could otherwise be generated by random noise.

Figure 24:
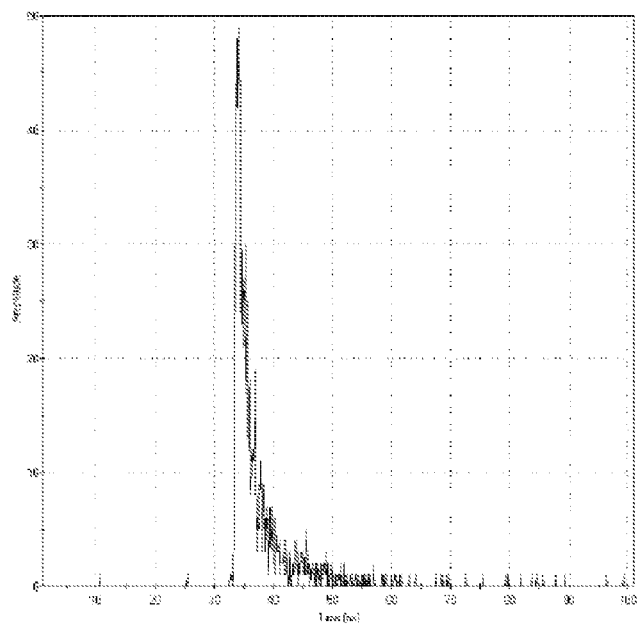
FIG. 24: Example time-count histogram representing PMT output at one Raman line of interest.

Counts resulting from detected Raman photons are accumulated in each of the observed time bins leading to the formation of a histogram (counts per time bin) that represents the time signature of observed PMT signals at a specific observation wavelength as illustrated in FIG. 24 (which shows counts on a scale from 0-50 vs. time on a scale from 0-100 ns).

Figure 25:
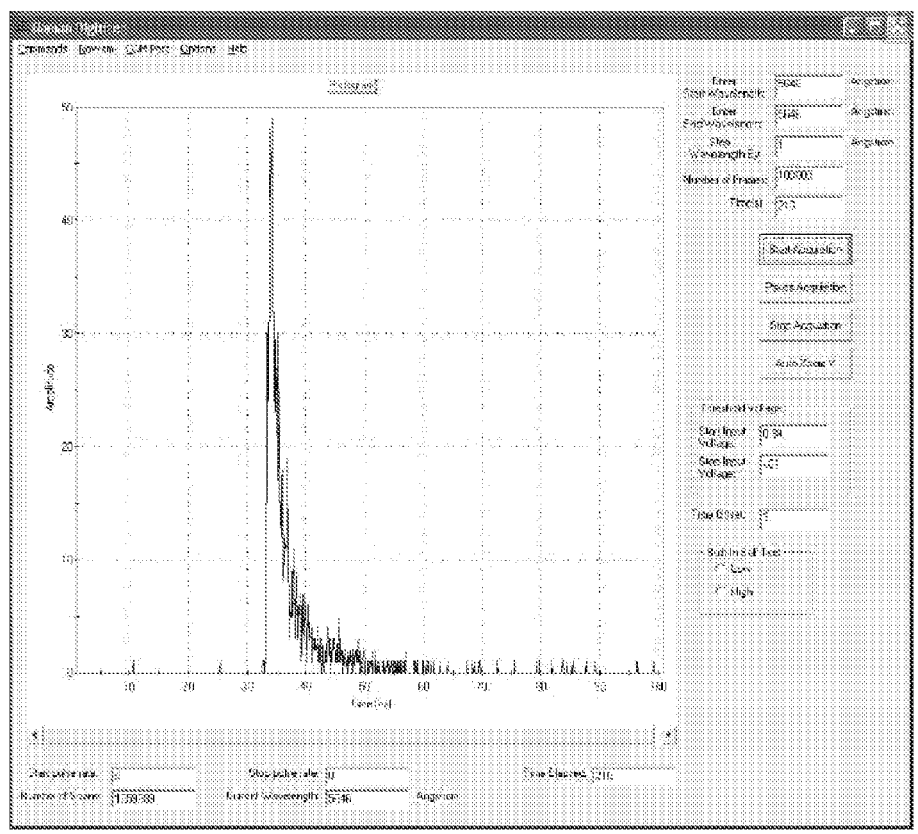
FIG. 25: Screenshot of the Data Acquisition User Interface according to another embodiment of the present invention.
Figure 26:
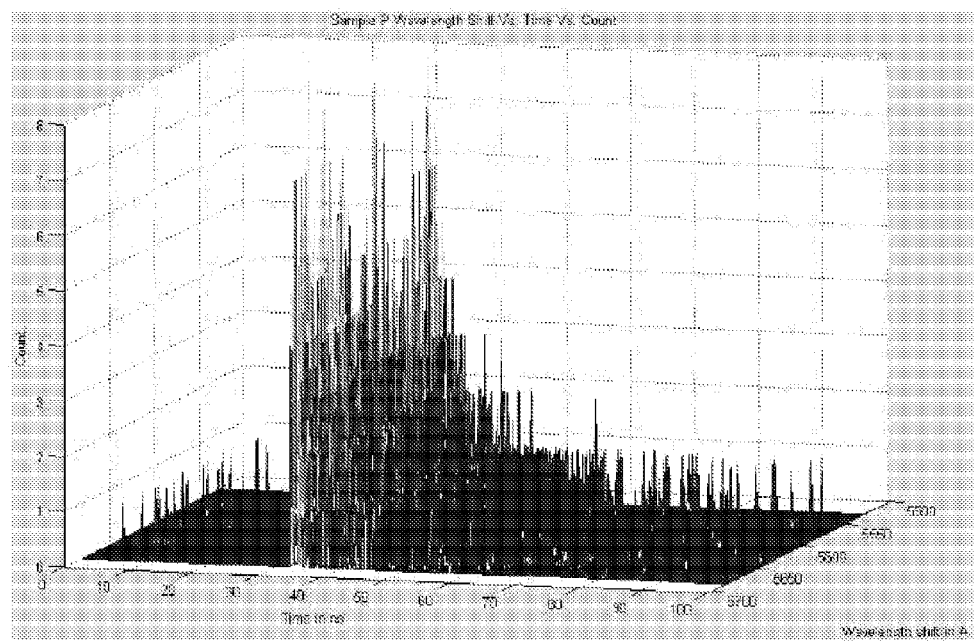
FIG. 26: Example of e-D time-count (Raman histogram and Raman spectrogram)-shift signature resulting from automated data acquisition at multiple wavelengths.

The high speed data acquisition capabilities of the PCI card were exploited through the development of automation software using the Visual Basic programming language that now enables computer controlled acquisition of a 3-D Raman scan (counts vs. time. vs. Raman shift) for any compound, effectively providing an automated interface between the system control computer, the Ortec 9353 PCI data acquisition card, and the CM-110 Monochromator. The user interface for this software is shown in FIG. 25 and an example 3-D Raman signature composed of multiple single-wavelength scans taken in succession is shown in FIG. 26 (in which the vertical scale represents count from zero to 8, the horizontal scale represents time in nanoseconds from 0-100, and the z/perspective scale represents wavelength shift in angstrom from 5700 to 5500). Note that the scaling of this chart does not limit the invention, the number of counts, the time scale, and the wavelength shift scale being factors of: the characteristics of the light pulse and the sample; cabling and sensor rise time; and the type of bonds in the sample; respectively, all by way of example only.

By creating an interface that communicates with the monochromator and PCI card simultaneously, the Raman measurement system thus described permits: running automated scans of samples using user-specified start and end wavelengths with a given increment at which to step from wavelength to wavelength; performing scans of user-specified duration to acquire data at each particular wavelength; running a scan of wavelengths as many times as the user desires without interaction. Separate and unique data files are created for each complete scan; creating a comma delimited output file of acquired data (shifts and photon counts); adjusting start and stop input voltage; and, graphing data collected during acquisition in real-time and updating the user on elapsed time.

A component-by-component sensitivity analysis was performed to ensure optimal alignment of the monochromator input and output slits, fiber position, probe location relative to the test cuvette, and PMT position on the exit slit of the monochromator. To facilitate this evaluation and optimization the benzene Raman line at 996 cm-1 was used a reference. At the outset of the optimization process benzene yielded a peak count of approximately 31+4 with a noise floor of approximately 6+2 and a 30 second run time. After completion of the parametric analysis, a count of 1640+50 was achieved with a noise floor of 23+4 and a similar 30 second run time, yielding an 18 fold improvement of signal-to-noise (roughly calculated as the mean Raman count/(mean noise+3σ)).

Figure 27:
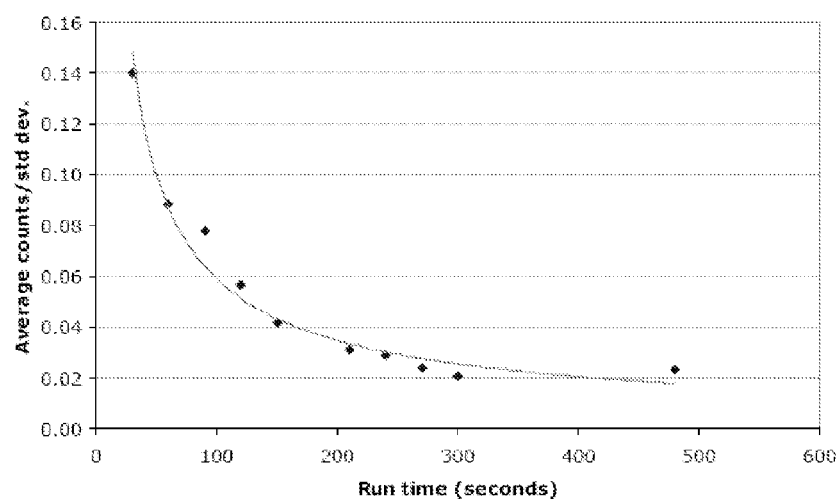
FIG. 27: Impact of run time on Raman count variability according to one embodiment of the present invention.

Analysis of counts obtained throughout the effort to optimize the optical path indicated that the test-to-test consistency of Raman counts at any given Raman line can depend upon test run time. To assess the relationship between run time and count variability a series of tests were run on the 1085 cm-1 line of a sample R oil (chosen at random). This analysis is summarized in FIG. 27, which shows improvement in data acquisition is obtained for a run time from three to five minutes in duration (240 seconds was chosen for tests performed subsequent to this analysis). Signal quality was evaluated using the ratio of the average counts achieved over 3 runs divided by the standard deviation of these counts. For times that exceed this range, little improvement in overall count variance is obtained between tests.

To assess the potential to employ the Raman sensor for the quantification of fatty acids in oils, a series of experiments were performed on twenty-three (23) oil samples. To provide an objective control for the experiments all of the oils were analyzed using gas chromatography. A summary of the oils evaluated in this program, and their respective fatty acid percentages as determined via GC analysis is provided in Table 1.

To address the key research questions outlined earlier three types of experiments were performed on the oil samples.

1. Broad spectrum, low-resolution scans of the oils to assess the general ability of system 50 to differentiate the oils.

2. Focused scans of the fatty acid spectral region (700-1200 $cm^{-1}$) of all oils to assess the distinguishing characteristics of this region in different oils and to assess the potential to directly quantify the presence of target fatty acids.

3. Calibration tests for select families of oils to identify specific Raman lines that can be used to reliably determine fatty acid concentrations.

Some of the parameters of all of these tests include the following. Two of the parameters pertain to the time domain: run time: the amount of time over which Raman counts are observed at any specific Raman line [in seconds]; and integration time: the amount of time over which bin counts in the acquired Raman histogram are integrated [nanoseconds (ns)].

In other parameter pertained to the frequency domain: step size: the amount by which the monochromator grating is advanced while scanning through the range of desired Raman frequencies [encoded in nanometers (nm), convertible to $cm^{-1}$] The approach and results for each of these test categories are described below.

Figure 28:
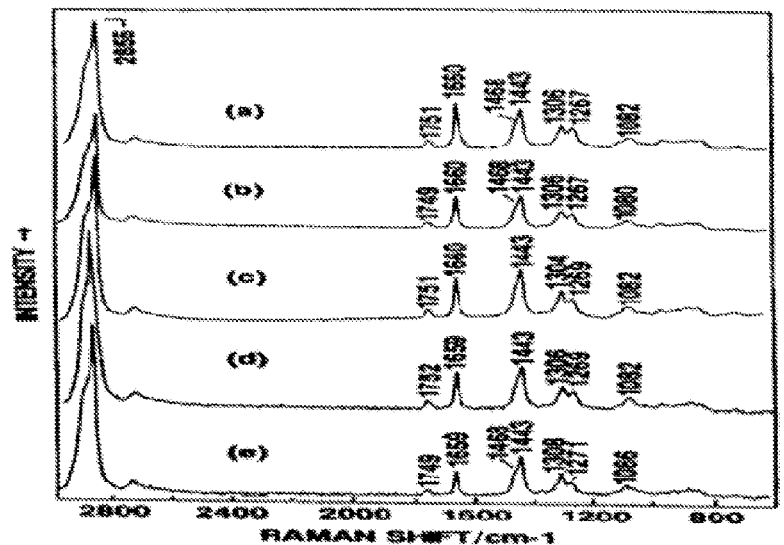
FIG. 28: Published oil signatures (a) sunflower (b) corn (c) sesame (d) grapeseed, and (e) olive oil.

Over a broad spectral range from approximately 600-2800 $cm^{-1}$, the primary vibrational modes (Raman characteristics) of oils are virtually identical as illustrated in FIG. 28. Very similar signatures were also achieved using the system 50 as illustrated for a limited number of samples in FIG. 29. The scans presented in this figure were obtained at low resolution (leading to some peak broadening and distortion) using about a 30 second count integration time, and were derived at the outset of the testing program before system optimization was complete. These scans to indicate that system 50 and 150 is indeed capable of seeing lines of interest, including the 1270-1310 $cm^{-1}$, 1440-1470 $cm^{-1}$, and 1650-1750 $cm^{-1}$ nominal bands. Note that the signatures presented in this report have been corrected for the non-linear gain characteristics of the detection photomultiplier tube in the spectral ranges of interest. No further effort was dedicated to refining these curves because scans of this large region are effectively non-descript. Instead, efforts were made to zoom-in on the range of Raman lines from 700-1200 $cm^{-1}$ which includes the primary vibrational modes of the target fatty acids (highlighted region in FIG. 29).

Figure 29:
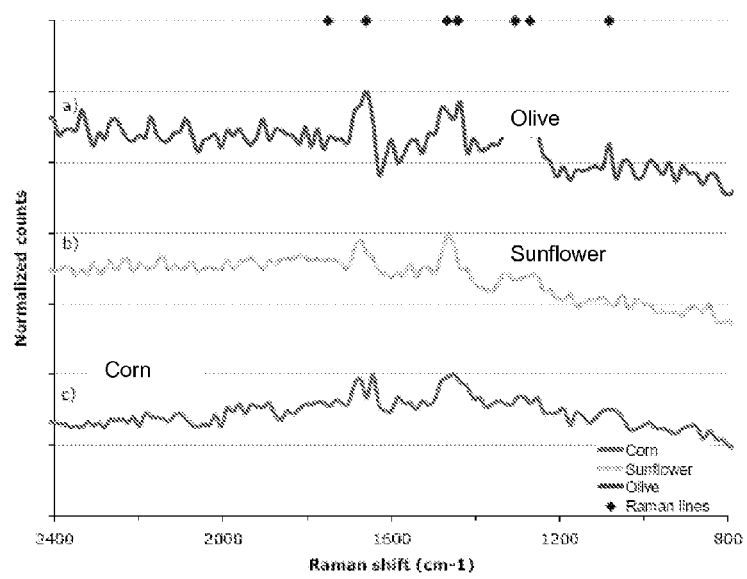
FIG. 29: Low resolution signatures obtained with a system according to one embodiment of the present invention: (a) olive (b) sunflower and (c) corn oil [30 second scans, 0.5 nm step size, 1.4 ns integration time]
Figure 30:
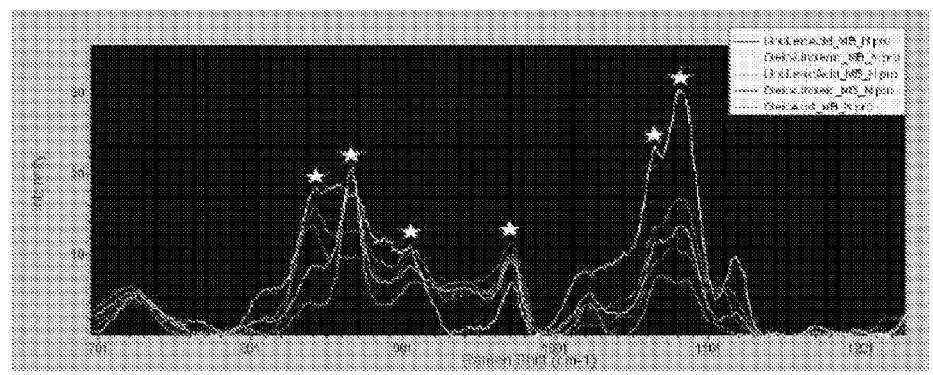
FIG. 30: Characteristic Raman signatures of unsaturated fatty acids including published data.
Figure 31A:
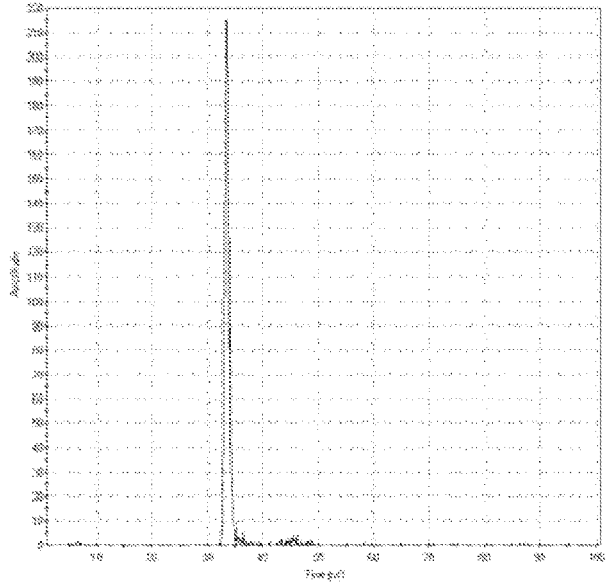
FIG. 31: Time-decay characteristics of (a) water Raman line at 3600 $cm^{-1}$, and (b) olive oil Raman line at 1085 $cm^{-1}$.
Figure 31B:
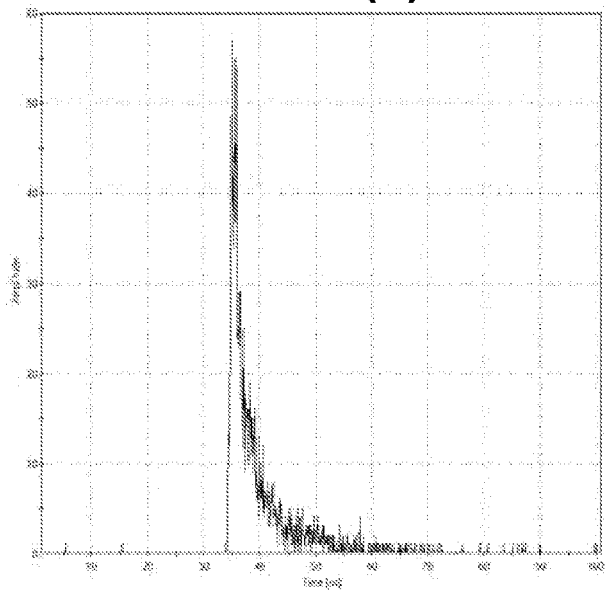

The fatty acids of interest, when analyzed independently, display vibrational lines within the region of 700-1200 $cm^{-1}$ as illustrated in FIG. 30 below. However, as illustrated in FIG. 29 above this spectral region is generally non-descript when examined for an oil. This observation is likely due to two factors. First, it is clear that all of the fatty acids of interest as well as several others (e.g., stearic, palmitic) are present simultaneously in an oil. This leads to a superposition of the independent signatures which makes the existence of individual Raman peaks less distinct. Secondly, it is also apparent that the oils, when interrogated with a laser source at 532 nm exhibit limited fluorescence, which, without optimized integration, further broadens the observed spectra. This latter point is illustrated in FIG. 31 below. In FIG. 31a, which presents the time decay characteristics of the water Raman line at 3600 $cm^{-1}$, it is apparent that the Raman return resulting from a laser pulse is essentially complete after approximately 3 ns. In contrast, FIG. 31b presents the time decay characteristics of the 1085 $cm^{-1}$ line of olive oil. Here it is seen that the return signal continues for nearly 20 ns, and the falling edge of the curve conforms to a classic exponential decay curve of the form $e^{-t/\tau}$, where $\tau$ is approximately 1.7 ns. Other samples exhibit decay constants in the range of 1.0 to 2.4 ns.

This limits the potential to directly correlate absolute Raman counts with the concentration of any individual fatty acid within an unknown oil. However, two approaches effectively assess unknown samples: (1) unknowns can be identified by general spectral patterns obtained via higher resolution scans and then Raman counts at key lines of interest can be directly linked to fatty acid concentration, and (2) multivariable fitting procedures can be used to simultaneously examine several Raman peaks based on signal superposition assumptions to back out the constituents of the oil under investigation.

Full scans of the fatty acid spectral region (700 $cm^{-1}$ to 1200 $cm^{-1}$) were undertaken for each of the 23 oils studied in this program. Representative signatures of each oil type are presented in FIG. 32 (note that grapeseed and sesame oils provided extremely high counts that require further interpretation and are thus not presented here). This data indicates that it is feasible to employ the general spectral fingerprint of an oil to determine its type. The curves differ both in general shape and in absolute intensity. All of these tests were run under identical conditions with a 30 second run time, 1.3 ns integration time and 0.2 nm step size. Each representative curve is the average of 3 scans.

Figure 32:
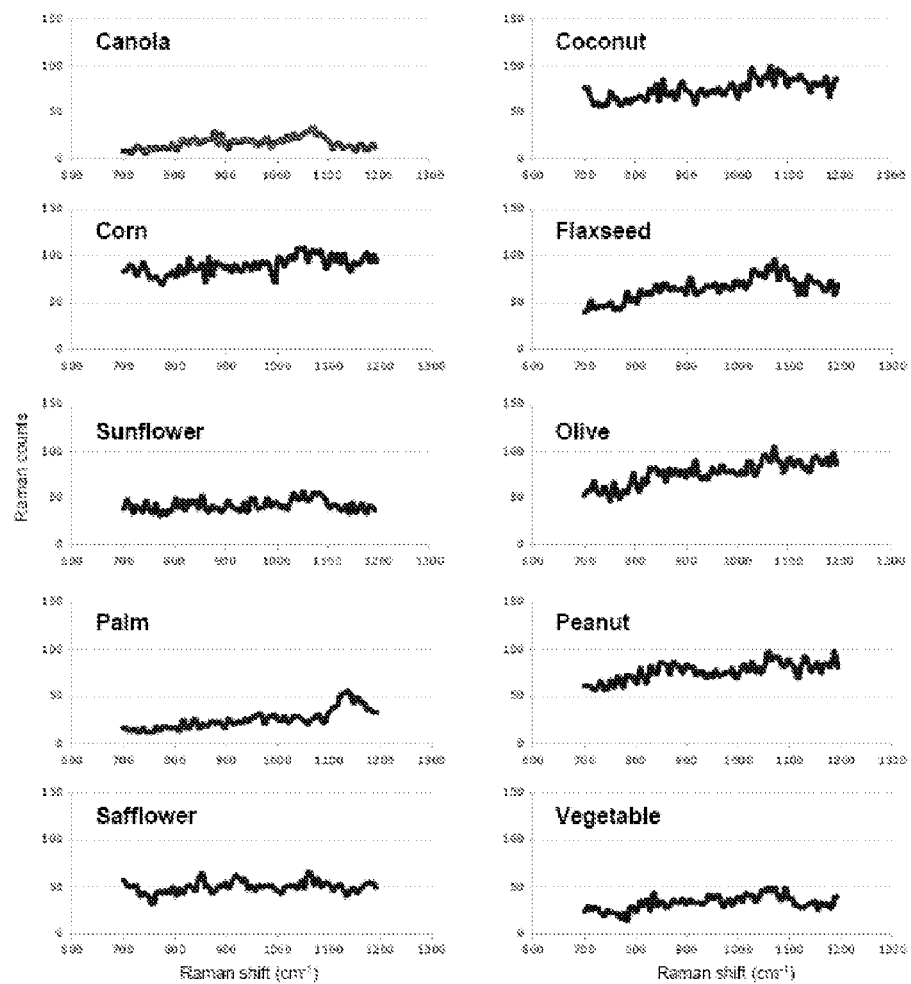
FIG. 32: Representative Raman signatures of primary oil types according to one embodiment of the present invention.
Figure 33A:
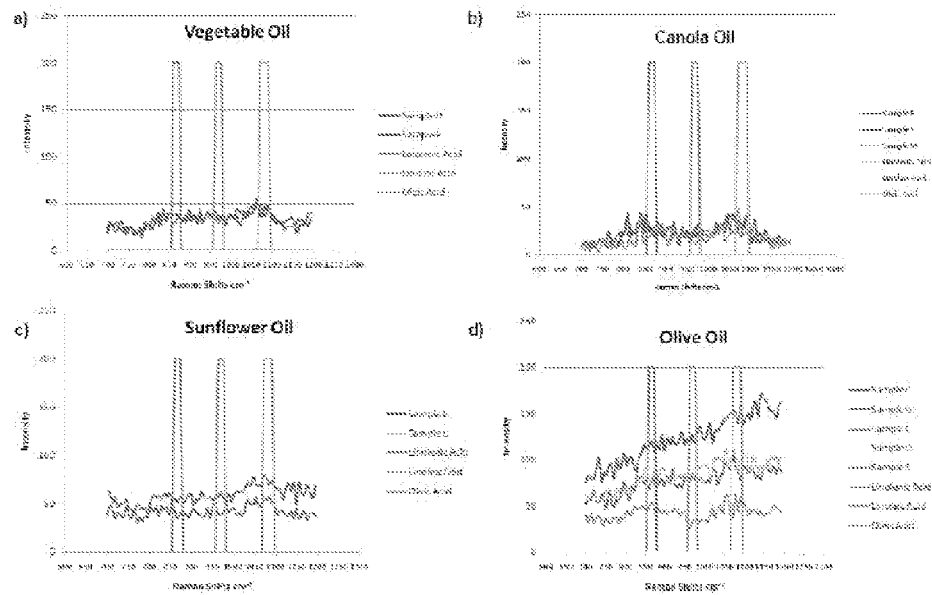
FIG. 33a: Characteristic Raman signatures of oil families obtained with a system according to one embodiment of the present invention [30 second run time, 1.3 ns integration time and 0.2 nm step size].
Figure 33B:
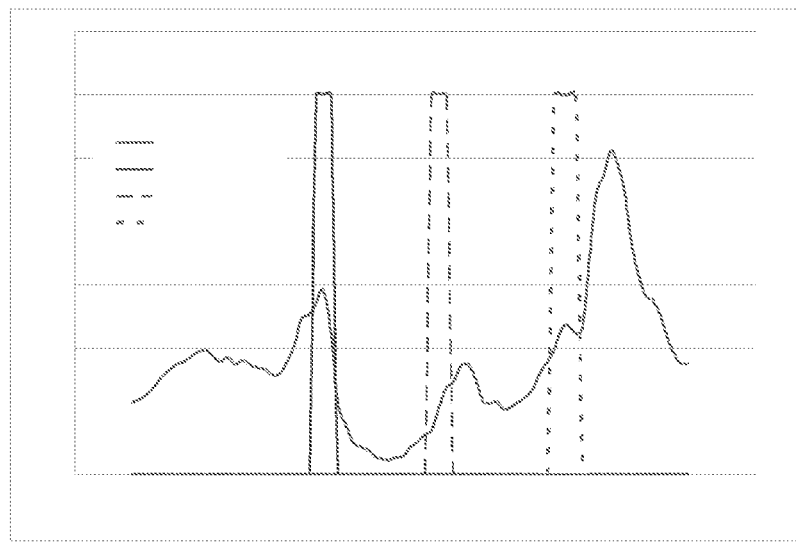
FIG. 33b: Characteristic Raman signature of canola oil obtained with a system according to another embodiment of the present invention.

For four of the oil types pictured in FIG. 32, more than one oil sample was available. Signatures for these oil families are provided in FIG. 33a (a to d). Each signature in these plots again represents the average of three scans run under identical conditions with a 30 second run time, 1.3 ns integration time and 2 nm step size. It is apparent from these signatures that the general spectral shape associated with any oil family is consistent. The locations of primary Raman lines for linolenic, linoleic and oleic acid are highlighted in each figure (865 $cm^{-1}$, 970 $cm^{-1}$ and 1085 $cm^{-1}$, respectively). However, in-family variations in the relative concentrations of core fatty acids lead to some spread in the absolute counts obtained for each sample. This issue is explored in further detail below. Also shown is FIG. 33b, which shows a Raman signature for one of the oil families, as measured by a measurement system according to another embodiment of the present invention.

Figure 34:
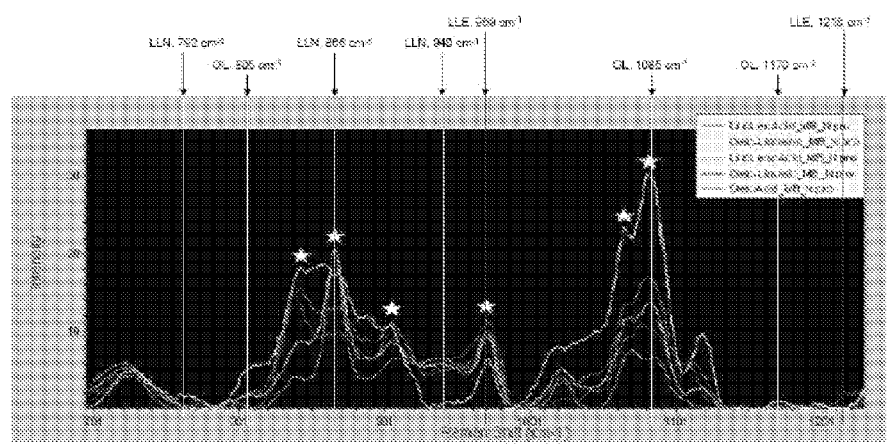
FIG. 34: Summary of measured Raman lines according to one embodiment of the present invention for oleic, linoleic, and linolenic acids and compared to the data of FIG. 30.

To assess the potential to perform quantitative analysis with the Raman system, samples within each of the oil families were analyzed at selected Raman lines deemed to be indicative of the presence of the target fatty acids and the results were compared to those obtained via GC analysis. The Raman shifts examined for each of the oils are summarized in FIG. 34 (which shows Raman shift lines superimposed on the data of FIG. 30). Each calibration test was run for 240 s (4 minutes), which as indicated earlier is in the optimal range for low variance counts.

Figure 35:
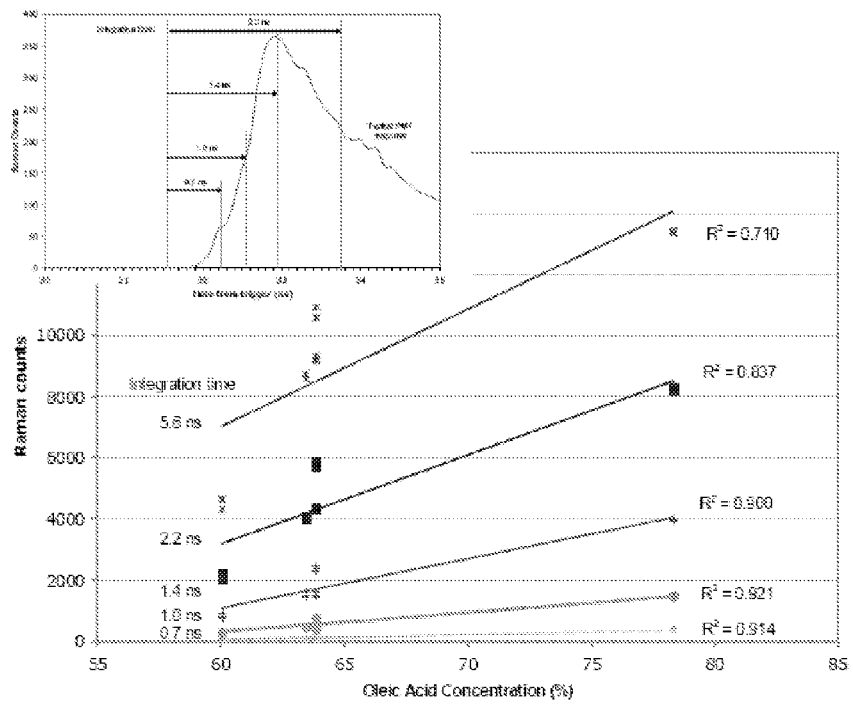
FIG. 35: Affect of integration time on Raman-GC correlation according to one embodiment of the present invention.

The quality of the relationship between Raman counts and GC test results is linked to the integration time used to interpret the test results (i.e., as mentioned earlier, the amount of time over which bin counts in the acquired Raman histogram are integrated). As shown in FIG. 35, which depicts the relationship between GC test results and Raman counts obtained for the 1170 $cm^{-1}$ Raman line for oleic acid in multiple tests performed on olive oil samples C, G, L, O and S, Raman counts acquired on the rising side of the PMT signal provide a strong linear relationship over the observed range of oleic concentrations to GC results. This relationship erodes as additional counts accumulate over time, and fluorescence begins to contribute to the return signal, showing evidence of the benefit of fluorescence rejection offered by time resolved counting.

The preferred relationships between Raman counts and GC results were observed for all lines of interest when the time-resolved Raman signatures were integrated for 1.0 ns. Note, however, that the linear regressions that were fitted to the data do not have zero intercepts and would display considerably lower R2 values (R2 being the coefficient of determination) if forced to intercept at a count equivalent to a similarly integrated 240 s dark count or noise floor. This observation has two primary implications: (1) the relationship between Raman counts and GC results provided by a direct correlation is locally linear, and thus for a finite range of potential fatty acid concentrations (as may be expected in food grade oils) is practical, and (2) the broader relationship between Raman counts and GC results is likely non-linear and/or a byproduct of multi-component influences that be disaggregated through techniques such as partial least squares analysis.

The insert graph in the upper left corner of FIG. 35 shows a typical response to PMT 700 as a function of time from the trigger signal provided by photodiode 300. For a PMT as described herein, the PMT signal begins to rise about 32 nanoseconds after the triggering signal from the photodiode. The PMT rise time can be seen to be about 10 nanoseconds, with the peak response appearing at about 33 nanoseconds. As shown in the inset of FIG. 35, one embodiment of system 50 includes a delay from the photodiode signal to the beginning of the integration time of about 31.5 nanoseconds. The effect of the integration period was measured for integration periods of 0.7, 1.0, 1.4, 2.2, and 5.6 nanoseconds, the corresponding counts and R2 being shown in the main plot of FIG. 35. It can be seen that there is a relatively high coefficient of determination for an integration time ending at about 1 nanosecond following the delay period. Therefore, in some embodiments of the present invention, it is advantageous to establish an integration period that achieves an acceptable R2 value for the particular photon counting sensor being utilized (which in some embodiments of system 50 is a photo-multiplier tube). In one embodiment, the integration period can be considered as a multiple of the rise time of the photon counter. In one embodiment, the integration period is less than about three times the rise time. However, to improve the R2 values, yet other embodiments include an integration period that ends proximate to the peak response of the photon counter. For a further improvement in the R2 coefficient determination, yet other embodiments of the present invention end the integration period prior to the peak response of the photon counter. In some embodiments, it may be helpful to determine the peak response of the particular photon counter during calibration testing. Although the inset of FIG. 35 shows the integration time starting prior to the initial response from the PMT 700, not all embodiments are so limited. In one embodiment, the integration period begins proximate to the first photons counted by the photon counter.

Figure 36:
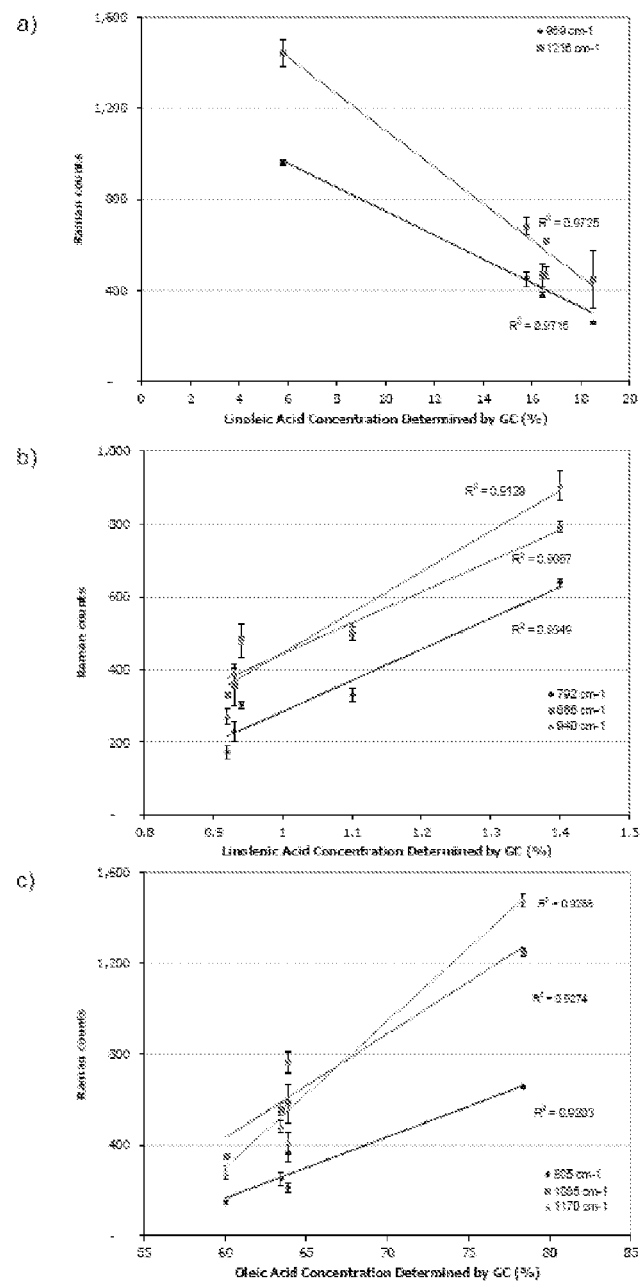
FIG. 36: Relationship between Raman counts and GC-derived fatty acid concentration in olive oil according to one embodiment of the present invention.
Figure 37:
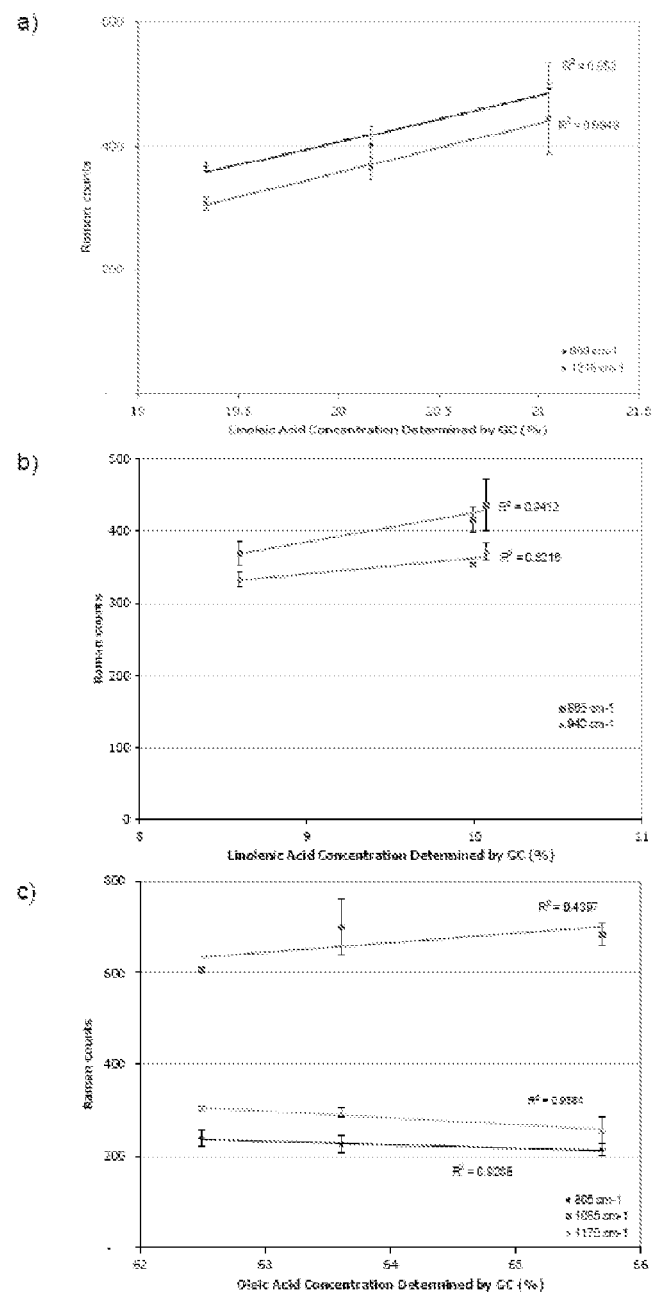
FIG. 37: Relationship between Raman counts and GC-derived fatty acid concentration in canola oil according to one embodiment of the present invention.

FIGS. 36 and 37 present the comparison of Raman counts versus GC (gas chromatograph) test results obtained for a range of Raman lines associated with each of the fatty acids of interest in olive and canola oils, respectively. Each of the data points presented represents the average of three Raman tests performed on the same sample with error bars that correspond to +1 standard deviation (samples C, G, L, O and S for olive oil, and samples F, J, and M for canola oil). Each test involved a run time of 240 seconds. For clarity of presentation, data are plotted at a horizontal coordinate that represents the average of pertinent GC results and error bars are not shown. Note that similar tests were also carried out on vegetable and sunflower oils, but they are not presented here since only two samples of each oil were available, obviously leading to a linear relationship.

Figure 38:
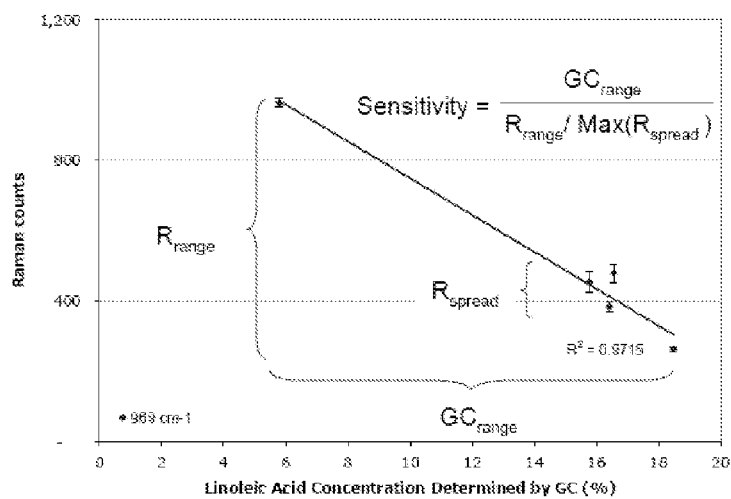
FIG. 38: A method according to another embodiment of the present invention regarding system sensitivity.

For olive oil, all of the analyzed lines display strong coefficients of determination exceeding 0.90, and the 792 cm$^{-1}$, 969 cm$^{-1}$, and 1170 cm$^{-1}$ lines appear to provide good sensitivity for linolenic, linoleic, and oleic acids, respectively. Sensitivity is determined by dividing the full range of GC-derived fatty acid percentage (GCrange), by the ratio full range of Raman counts (Rrange) to the maximum Raman count spread (Rspread) at any given GC-derived fatty acid concentration. This concept is illustrated in FIG. 38. Using this approach, it can be inferred that the Raman system can differentiate 0.2% variations in linolenic acid, 2.5% variations in linoleic acid, and 5.4% in oleic acid in olive oils. Separation of these influences via a method such as partial least squares or other data processing methods enables further improvement.

For canola oil, there is greater spread in the data; however coefficients of determination relating Raman counts to GC results remain above 0.82 for the majority of the studied Raman lines (with the exception of the 1085 cm-1 line). More specifically, the 866 cm-1, 969 cm-1, and 1170 cm$^{-1}$ lines appear to provide the best sensitivity for linolenic, linoleic, and oleic acids, respectively. Here, it can be inferred that the Raman system can differentiate 1.2% variations in linolenic acid, 1.1% variations in linoleic acid, and 4.1% in oleic acid in canola oils.

While the inventions have been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A method for determining the composition of a sample, comprising:
    providing a controller and a source of pulsed light and a sensor receiving photons and providing an electrical signal corresponding to each received photon;
    repetitiously illuminating the sample with a pulse of light from the source, wherein some of the source photons from each pulse are scattered by the sample;
    substantially eliminating the elastically scattered photons and collecting the Raman-shifted inelastically scattered photons;
    preparing a time histogram of the number of collected Raman-shifted photons, the histogram dividing a predetermined period of time into a plurality of counting bins arranged in sequential order, each bin containing a natural number corresponding to the number of Raman-shifted photons collected during the corresponding time interval, one of the bins having the largest natural number; and
    determining by the controller the composition of the sample by analyzing the photons collected earlier in time than the one bin and ignoring the photons collected later in time than the one bin.

2. The method of claim 1 which further comprises starting the period of time after a predetermined delay time, the delay time corresponding to transmission delays associated with the sensor.

3. The method of claim 2 wherein said providing includes a second sensor providing a second electrical signal corresponding to the receipt by the second sensor of a photon, and which further comprises:
    splitting the pulse;
    directing a split portion of the pulse to the second sensor; and
    beginning the delay time by the second electrical signal.

4. The method of claim 1 which further comprise beginning the period of time by the counting of a photon by the sensor.

5. The method of claim 1 wherein the source of light is a Q switched laser.

6. The method of claim 1 wherein the sensor is a photomultiplier tube.

7. The method of claim 1 wherein the source is a monochromatic source of coherent light.

8. The method of claim 1 wherein the source of light is monochromatic with a wavelength more than about 500 nanometers and less than about 600 nanometers.

9. The method of claim 1 which further comprises rejecting the scattered photons that are not within a predetermined frequency band before said counting.

10. The method of claim 1 wherein the source is a monochromatic source, said collecting is at a first frequency, and which further comprises:
    illuminating the sample with a second pulse of light having a beginning and an ending, wherein some of the source photons of the second pulse are scattered by the sample;
    substantially eliminating the elastically scattered photons and collecting the inelastically scattered photons of the second pulse at a second frequency different than the first frequency;
    counting the Raman-shifted inelastically scattered photons by the sensor at the second frequency during a second predetermined period of time; and
    stopping said counting before collecting a statistically significant sample of non-Raman shifted photons.

11. The method of claim 1 wherein the period of time is less than about six times the period of the pulse.

12. The method of claim 1 which further comprises not counting Raman-shifted inelastically scattered photons that have a frequency that is less than a first lower frequency or greater than a second higher frequency.

13. The method of claim 1 wherein the sensor converts each collected photon to a corresponding electrical signal, and which further comprises not counting a photon if the magnitude of the corresponding electrical signal does not exceed a predetermined intensity threshold.

14. The method of claim 1 wherein said eliminating includes eliminating anti-Stokes shifted inelastically scattered photons and said collecting is of Stokes-shifted inelastically scattered photons.

15. An apparatus for determining the composition of a sample comprising:
- a repetitive source of pulsed light at a source wavelength;
- a chamber for receiving the sample;
- a probe for directing the pulsed light onto the sample and collecting the photons scattered by the sample;
- a controllable photon filter receiving the collected photons and substantially eliminating photons not within a selectable frequency band defined between a first selectable lower frequency and a second selectable higher frequency, the photon filter substantially eliminating photons at the source wavelength;
- an electrical filter having an intensity threshold;
- a photon counting sensor for receiving Raman-shifted inelastically scattered photons from said photon filter and providing a plurality of electrical signals each in response to a different one of the corresponding plurality of received photons, said sensor further counting only the photons within the frequency band having corresponding electrical signals that exceed the intensity threshold of the electrical filter; and
- a controller having a plurality of memory bins and being operably connected to said source, said filter, and said sensor;
- wherein said controller receives the count of photons from a first pulse, stores the count as a first count signal in a first memory bin associated with the first frequency band.

16. The apparatus of claim 15 wherein said photon filter is an electronically controllable monochromator.

17. The apparatus of claim 15 wherein the count signal comprises the counting of individual photons as a function of time.

18. The apparatus of claim 15 wherein the count signal is a natural number.

19. The apparatus of claim 15 wherein the count signal is acquired during a period of summation, and the period ends before the receipt of a statistically significant quantity of fluorescence photons or phosphorescence photons on said sensor.

20. The apparatus of claim 19 wherein said sensor has a rise time and a peak in response to receiving a photon, and the period of summation ends before the peak.

21. The apparatus of claim 19 wherein said sensor has a rise time in response to receiving a photon, and the period of summation ends during the rising period.

22. The apparatus of claim 19 wherein the period of summation is triggered by the receipt of photons by the sensor.

23. The apparatus of claim 15 wherein said source is a monochromatic Q switched laser.

24. The apparatus of claim 23 wherein said laser emits light having a wavelength greater than about 500 nanometers and less than about 600 nanometers.

25. The apparatus of claim 15 wherein said probe includes a first optical path for providing the light onto the sample and a second optical path for collecting the scattered photons, the second optical path including a long-pass filter.

26. The apparatus of claim 15 wherein said source includes a beam splitter, and the pulsed signal is a split portion of the pulse of light.

27. The apparatus of claim 26 wherein said controller receives a split portion of the pulse of light, said controller beginning a period of summation corresponding to receiving the split portion of light, the count signal being acquired during the period of summation.

28. The apparatus of claim 15 wherein the pulsed signal corresponds to the start of the pulse, said controller being operably coupled to said source and receiving the pulsed signal, said controller beginning a period of summation corresponding to receiving the pulsed signal, the count signal being acquired during the period of summation.

29. The apparatus of claim 15 wherein the count signal is acquired during a period of summation, the pulse of light has a time width, and the period of summation is greater than about four times the time width of the pulse.

* * * * *